United States Patent
Manders et al.

(10) Patent No.: US 12,191,001 B2
(45) Date of Patent: Jan. 7, 2025

(54) POPULATION FREQUENCY MODELING FOR QUANTITATIVE VARIANT PATHOGENICITY ESTIMATION

(71) Applicant: Laboratory Corporation of America Holdings, Burlington, NC (US)

(72) Inventors: Toby Manders, San Francisco, CA (US); Keith Nykamp, Berkeley, CA (US); Alexandre Colavin, San Diego, CA (US); Yuya Kobayashi, Menlo Park, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 18/700,257

(22) PCT Filed: Oct. 31, 2023

(86) PCT No.: PCT/US2023/036543
§ 371 (c)(1),
(2) Date: Apr. 10, 2024

(87) PCT Pub. No.: WO2024/097261
PCT Pub. Date: May 10, 2024

(65) Prior Publication Data
US 2024/0339177 A1    Oct. 10, 2024

Related U.S. Application Data

(60) Provisional application No. 63/421,430, filed on Nov. 1, 2022.

(51) Int. Cl.
*G16B 40/00* (2019.01)
*G16B 20/40* (2019.01)

(52) U.S. Cl.
CPC ............. *G16B 40/00* (2019.02); *G16B 20/40* (2019.02)

(58) Field of Classification Search
CPC .................. G16B 40/00; G16B 20/40
(Continued)

(56) References Cited

U.S. PATENT DOCUMENTS

| 8,744,982 B2 * | 6/2014 | Crockett | G16B 40/00 |
| | | | 706/45 |
| 2013/0116930 A1 * | 5/2013 | Karczewski | G16B 20/20 |
| | | | 702/19 |

(Continued)

FOREIGN PATENT DOCUMENTS

| WO | WO-2012155148 A2 * | 11/2012 | G06F 19/24 |
| WO | WO-2016209999 A1 * | 12/2016 | G06F 19/24 |

(Continued)

OTHER PUBLICATIONS

International Application No. PCT/US2023/036543, International Search Report and Written Opinion dated Feb. 15, 2024.

(Continued)

*Primary Examiner* — Michael Tomaszewski
(74) *Attorney, Agent, or Firm* — NICHOLSON DE VOS WEBSTER & ELLIOTT LLP

(57) ABSTRACT

Embodiments of the disclosed technologies apply a logistic regression model to a set of population data for a set of genes. The set of population data includes a set of features for a variant located at a position within a gene. The set of features includes at least one population frequency meta-feature. The at least one population frequency meta-feature quantifies predictive value of allele frequency in the gene. Using the first set of population data, a variant classification prediction output by the logistic regression model is evaluated based on an expected variant classification. The logistic (Continued)

regression model is adjusted until at least one first performance criterion is satisfied to produce a trained logistic regression model. The trained logistic regression model is capable of outputting variant pathogenicity estimates that satisfy at least one second performance criterion.

48 Claims, 15 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 2013/0116931 | A1* | 5/2013 | Karczewski | G16B 40/20 |
| | | | | 702/19 |
| 2014/0359422 | A1* | 12/2014 | Bassett, Jr. | G16B 20/00 |
| | | | | 707/754 |
| 2016/0371431 | A1* | 12/2016 | Haque | G06N 7/01 |
| 2019/0172556 | A1* | 6/2019 | Karczewski | G16B 20/30 |
| 2020/0111109 | A1* | 4/2020 | Lei | G06N 3/08 |
| 2020/0279157 | A1* | 9/2020 | Gao | G16B 40/20 |
| 2022/0027388 | A1* | 1/2022 | Gao | G06F 16/285 |
| 2022/0028485 | A1* | 1/2022 | Gao | G16B 40/00 |
| 2022/0189581 | A1* | 6/2022 | Neville | G16B 20/00 |
| 2022/0375609 | A1* | 11/2022 | Guo | C12N 15/90 |
| 2023/0420073 | A1* | 12/2023 | Bui | G06N 5/022 |

FOREIGN PATENT DOCUMENTS

| | | | | |
|---|---|---|---|---|
| WO | WO-2022024221 | A1 * | 2/2022 | G06N 3/0464 |
| WO | WO-2024097261 | A1 * | 5/2024 | |

OTHER PUBLICATIONS

Da Rocha, Jorge E.B. et al., "The Extent and Impact of Variation in ADME Genes in Sub-Saharan Africa Populations," Frontiers in Pharmacology, vol. 12, Article 634016, Apr. 28, 2021.

Keerthi S. Sathiya et al., "A Modified Finite Newton Method for Fast Solution of Large Scale Linear SVMs," Journal of Machine Learning Research, vol. 6, No. 12, pp. 341-361, Mar. 2005.

Lai, Carmen et al., "LEAP: Using Machine Learning to Support Variant Classification in a Clinical Setting," Human Mutation, vol. 41, No. 6, pp. 1079-1090, Jun. 2020.

* cited by examiner

| Population Modeling | | |
|---|---|---|
| Population modeling evidence | Sherloc Points | Accuracy |
| Very highly predictive benign score | 5B | >99% NPV |
| Highly predictive benign score | 3B | >99.5% NPV |
| Moderately predictive benign score | 1B | >80% NPV |
| Moderately/Highly predictive pathogenic score | 1P | >80% PPV |

Benign | Likely benign | Variants of uncertain significance | Likely pathogenic | Pathogenic Population data — Informative for ruling out the possibility that a variant can cause a rare disease Variant type — Help identify variants that are likely to be pathogenic Clinical observations — Critical for demonstrating a direct link between a variant and a disease Experimental studies — Useful for assessing the functional impact of a variant Indirect and computational — Supports other lines of evidence 5B    3B    4P  5P

FIG. 8F

POPULATION FREQUENCY MODELING FOR QUANTITATIVE VARIANT PATHOGENICITY ESTIMATION

CROSS-REFERENCE TO RELATED APPLICATION

This application is a national stage of International Application No. PCT/US2023/036543 filed Oct. 31, 2023, which claims the benefit of and priority to U.S. Provisional Patent Application No. 63/421,430 filed Nov. 1, 2022, each of which is incorporated herein by this reference in its entirety.

TECHNICAL FIELD

A technical field to which this application relates is genetic testing. Another technical field to which this application relates is machine learning-based variant classification systems.

BACKGROUND

Genetic variants are differences in DNA sequences between individuals in a population. There are many different types of variants, including structural variations, single-nucleotide polymorphisms, insertion and deletion variations, copy number variations, and translocations and inversions.

Genetic sequencing technology continues to evolve rapidly. High-throughput sequencing technologies increasingly enable genetic testing spanning genotyping, single genes, gene panels, exomes, genomes, transcriptomes and epigenetic assays for genetic diseases. The increased complexity of analysis and interpretation of clinical genetic testing, and the increased volume of testing, have been accompanied by new challenges in the interpretation of sequence variants.

For example, clinical molecular laboratories are increasingly detecting novel sequence variants in the course of testing patient specimens for a rapidly increasing number of genes associated with genetic diseases. While some phenotypes are associated with a single gene, many are associated with multiple genes.

Variant classification refers to a process of classifying genetic variants based on evidence supporting or rejecting a causal relationship with disease. The clinical significance of any given sequence variant falls along a gradient, ranging from those in which the variant is almost certainly pathogenic for a disease to those that are almost certainly benign.

Variant classifications are not themselves diagnoses, but can be used by clinicians to make diagnostic decisions.

BRIEF DESCRIPTION OF THE DRAWINGS

The disclosure will be understood more fully from the detailed description given below and from the accompanying drawings of various embodiments of the disclosure. The drawings are for explanation and understanding only and should not be taken to limit the disclosure to the specific embodiments shown.

FIG. 8F illustrates another example of population frequency modeling results for a population frequency model configured using a logistic regression model, integrated with a variant classification framework in accordance with some embodiments of the present disclosure.

DETAILED DESCRIPTION

Figure 1:
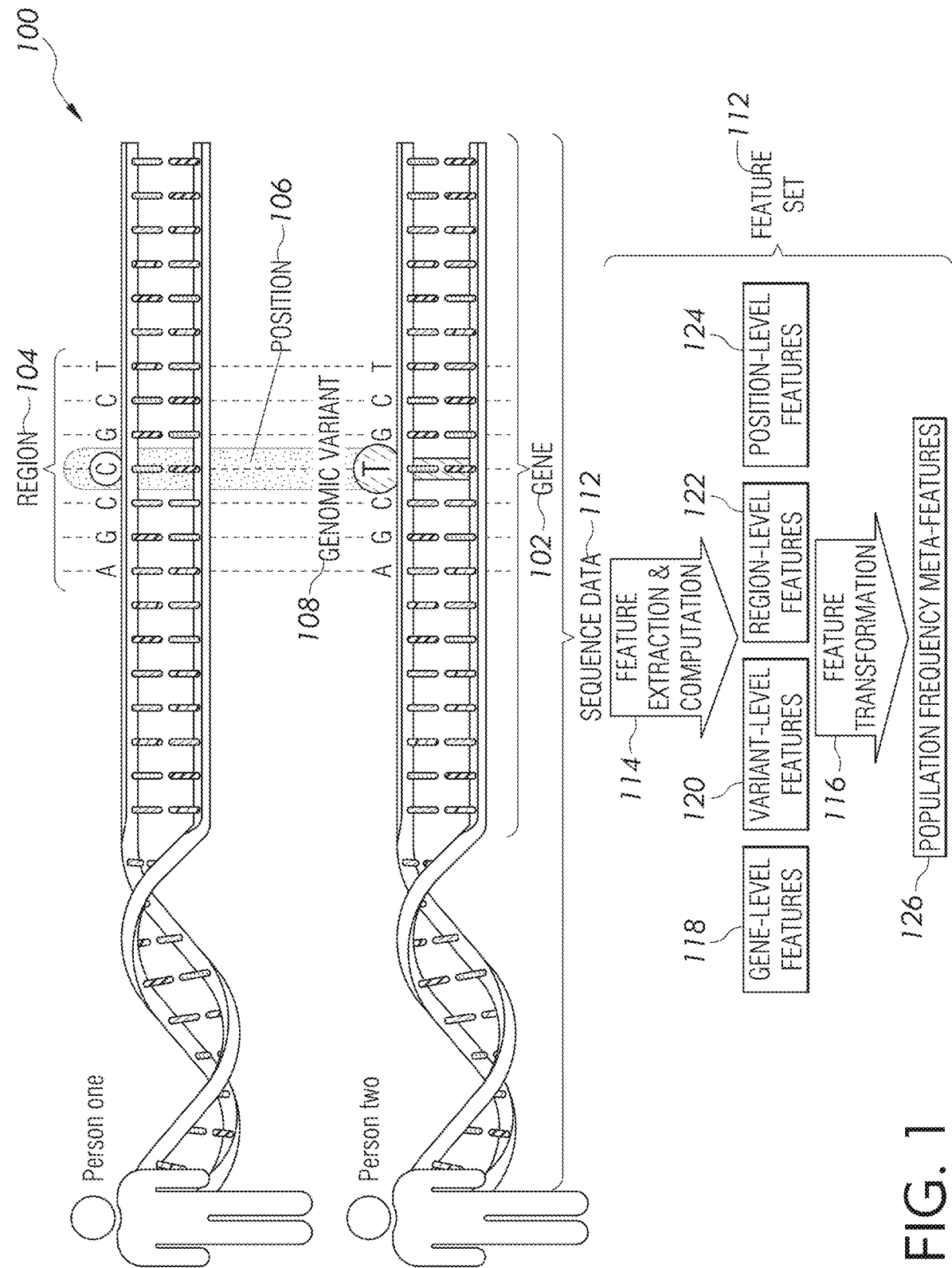
FIG. 1 illustrates an example of a feature generation process for machine learning-based population frequency modeling, in accordance with some embodiments of the present disclosure.

Given a gene, a particular genetic disease, and a population, there are features of the gene-disease relationship that are associated with the frequency of pathogenic variants in the population. These features include penetrance, age-of-onset, severity, inheritance pattern, and disease prevalence. Prevalence may refer to the allele frequency, in a generally healthy population, of a variant that is potentially associated with a genetic disorder, or to the frequency of patients affected with a disease in a given population.

Given a disease, a greater than expected prevalence of a variant in a population is a pattern that has been empirically observed as constituting evidence for a benign classification with respect to the disease, or conversely, that a lower than expected prevalence should be considered evidence for a pathogenic classification with respect to that disease. According to the American College for Medical Genetics (ACMG) guidelines for the interpretation of sequence variants, given a disorder, a variant present in a population more frequently than the prevalence of the disorder should constitute strong evidence for a benign classification.

However, the prevalence of pathogenic variants in large populations is the outcome of a complex interplay of various gene-disease attributes that reflect the genetic makeup of individuals for whom sequencing data are available. As a result, accurately and systematically defining the relationship between allele frequency and pathogenicity with respect to a given population and disease has been an ongoing challenge across all gene-disease relationships. A challenge is how to define and calculate the greater-than-expected boundary that should be used to classify a particular variant as benign with respect to a given disease based on population frequency data. Another challenge is to improve upon the conventional binary classification approaches.

The Genome Aggregation Database (gnomAD) is a large population database that has been developed by an international coalition with the goal of aggregating and harmonizing exome and genome sequencing data from a wide variety of large-scale sequencing projects, and making summary data available for the wider scientific community. For example, the gnomAD v2.1.1 data set spans 125,748 exome sequences and 15,708 whole-genome sequences from unrelated individuals sequenced as part of various disease-specific and population genetic studies. Subsequent versions of gnomAD include even more genomes and even greater diversity of ancestries.

A major, industry-wide challenge of using general population frequency data obtained from large general population databases, such as gnomAD, to classify variants is that many of the attributes that have been conventionally considered to be key predictive features are hard to obtain and not straightforward to interpret. For example, penetrance is difficult to measure accurately, is often unavailable, and can vary from variant to variant. Age-of-onset is rarely a single value but more typically a range of values. Severity is typically a qualitative, not quantitative, measure. Prevalence is often inaccurate or imprecise and can vary from one ancestry group to another.

Moreover, gene-level measurements only provide information about the cumulative frequency of all pathogenic variants in a specific gene, and do not provide information about specific, individual variants in that gene. For example, a prevalence of 0.1% could mean that there is one pathogenic variant in the gene with an allele frequency of 0.1%, or that there are 1,000 different pathogenic variants, each having an allele frequency of 0.0001%, or any other combination of pathogenic variants that adds up to 0.1%. The differences in the distributions of pathogenic variants have very different implications for how population allele frequency data should be used in variant classification, giving rise to the need for further refinement.

Another limitation of conventional approaches, which is overcome by the described population frequency modeling approach, is that large population databases such as gnomAD only include data that are estimates of the true population frequency of various variants; as a result, there is sampling uncertainty around those estimates. That sampling uncertainty is accounted for by the described feature generation approaches applied to large population data for variant classification as described herein.

Notwithstanding these and other limitations, the conventional methodologies for assessing this type of allele frequency data have relied heavily on the aforementioned gene-disease attributes. As a result, genetic testing labs have had to conservatively set high discrete allele frequency thresholds for classifying variants, and then broadly apply these conservative thresholds to large groups of genes based on simple parameters (e.g., thresholds for genes associated with dominant diseases versus thresholds for genes associated with recessive diseases). Consequently, labs have not been able to fully leverage the allele frequency data available in these large population databases for variant classification. This has resulted in too many variants being classified as variants of uncertain significance (VUS) even when the available allele frequency data suggests that the variants are too common to be expected to cause disease. In these instances, patients may be left with uncertainty about how their genetic testing results reflect their disease risk or diagnosis, and how those results should influence their care.

The complexities and limitations in both the current state of research on a given gene-disease pair and the relationships among the gene-disease attributes have curtailed the use of quantitative algorithms for variant classification. The disclosed approach addresses these and other challenges in variant classification. Embodiments of the disclosed approach apply machine learning techniques to develop a computational algorithm into a machine learning model for population frequency modeling. The described population frequency model uses logistic regression to quantitatively estimate the probability of a variant's pathogenicity based on allele frequency data obtained from large population databases, such as gnomAD.

Certain embodiments of the described population frequency model examine allele frequency in the context of a relatively small set of attributes that are not among the gene-disease attributes mentioned above. Embodiments avoid using those aforementioned gene-disease attributes as features and instead have engineered particularly useful combinations of other variant-, gene-, and/or position level properties of a given variant. For example, embodiments of the described population frequency model have been shown to generate reliable pathogenicity estimates based on a combination of allele frequency and a total of less than thirty other input features. For instance, the number of input features is in the range of about twenty features to about thirty features, in some embodiments. The combination of features engineered as described herein enables embodiments to exclude the aforementioned gene-disease attributes from the feature set that is used to configure the population frequency model.

Rather than relying on gene-disease attributes, the population frequency model resulting from application of the described approaches leverages the expected frequency distributions of known benign and known pathogenic variants within a given gene, thereby allowing for a quantitative assessment of how much a specific variant's allele frequency deviates from what would be expected if the variant were pathogenic. Using the described approach, the model calculates and outputs a probability of pathogenicity for each variant.

Unlike prior approaches that are not quantitative, the population frequency model configured as described maps a continuous measurement (e.g., allele frequency) to a continuous outcome (e.g., a probability of pathogenicity). For example, embodiments of the population frequency model can provide a variant-specific quantitative measure of population frequency as a continuous score. Moreover, embodiments of the population frequency model allow for a continuous quantitative scoring approach alternatively or in addition to a binary approach.

The output of the population frequency model can be used directly for variant classification or can be supplied as an input to a variant classification framework. For example, the model output can be incorporated into the population data portion of the Sherloc framework. The Sherloc framework is a semi-quantitative method for variant interpretation (i.e., a process for reviewing and evaluating evidence of pathogenicity, classifying variants, and communicating pathogenicity information to patients in an understandable way, which is also used for classifying variants). Experimental results have shown that when the model output produced in accordance with the disclosed approaches is provided as an input to the Sherloc framework, the number of variants that conventionally would have been classified as VUS due to a paucity of other evidence is reduced.

Without any information about complex gene-disease attributes, a population frequency model configured as described has been able to reproduce expected relationships between genes with different gene-disease attributes despite those attributes not being included in the set of features provided to the model as model inputs. Using the gene-disease attribute of inheritance pattern as an example, a gene associated with a recessive condition is generally expected to have a higher prevalence of pathogenic variants than a gene associated with a dominant condition. This is because heterozygous carriers of autosomal recessive conditions are expected to be part of the population database cohort, whereas individuals with one pathogenic variant in autosomal dominant conditions are likely to be affected by disease, thus resulting in their exclusion. Consequently, even if two variants have the same allele frequency, the one observed in the recessive gene is more likely to be pathogenic than the one observed in the dominant gene.

Figure 8A:
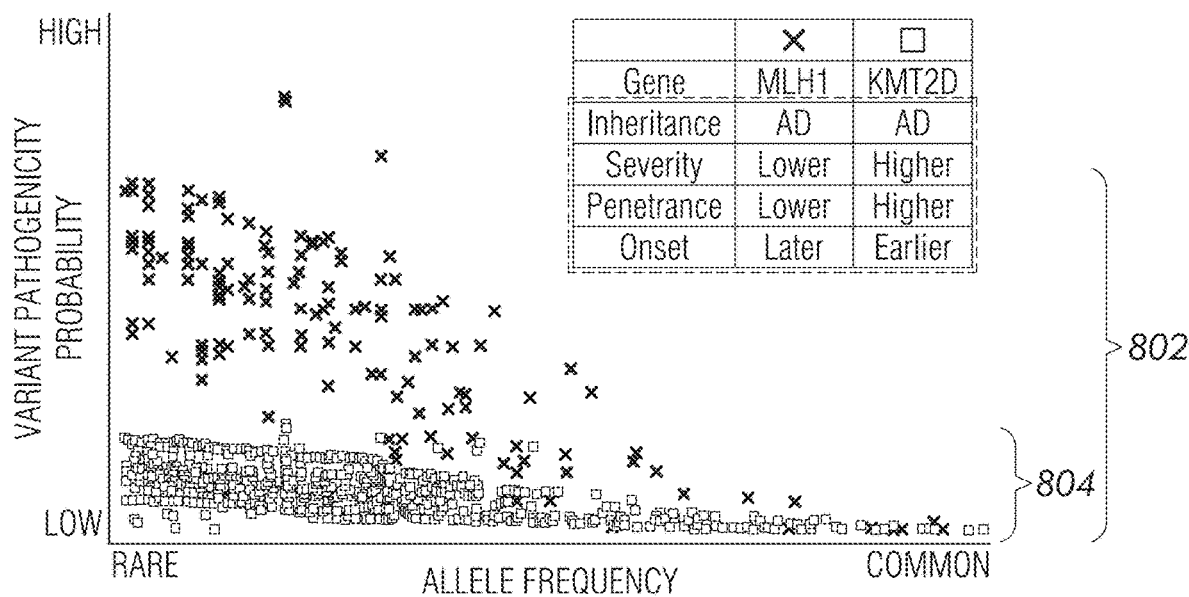
FIG. 8A illustrates an example of population frequency modeling results for a population frequency model configured using a logistic regression model, in accordance with some embodiments of the present disclosure.
Figure 8B:
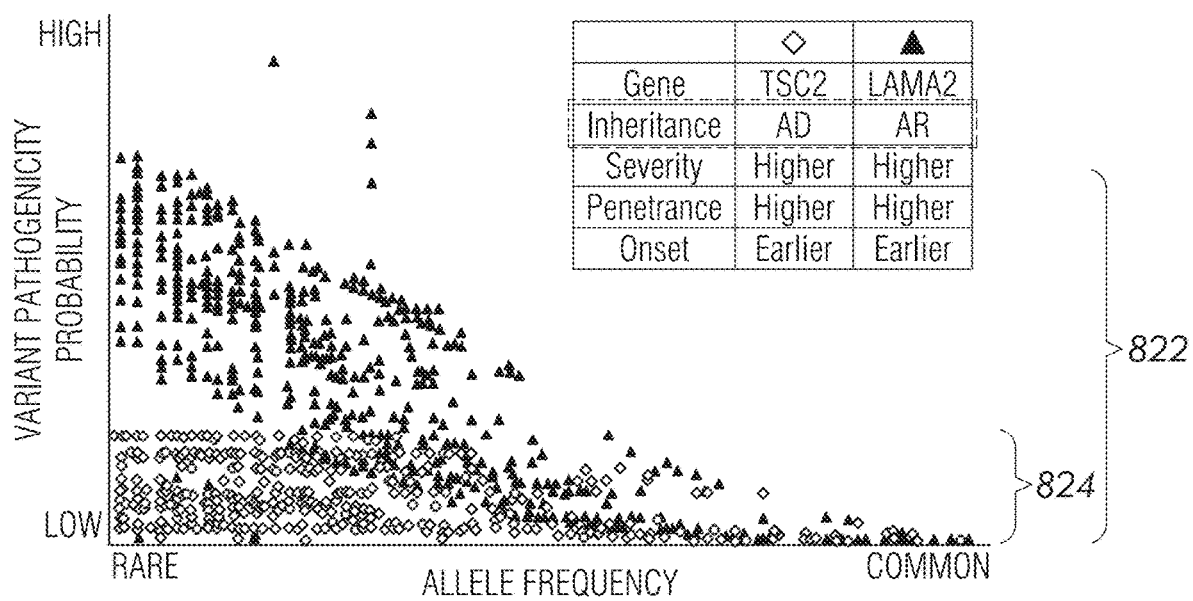
FIG. 8B illustrates another example of population frequency modeling results for a population frequency model configured using a logistic regression model, in accordance with some embodiments of the present disclosure.

As described in more detail below, when an embodiment of the described population frequency model has been implemented in two such genes, without any prior information on inheritance patterns, the model has reported a higher probability of pathogenicity for variants in the gene associated with the autosomal recessive condition than for those in the gene associated with the autosomal dominant condition (e.g., LAMA2 versus TSC2). For example, FIG. 8B shows results that demonstrate that embodiments of the described population frequency model can discern the effects of different inheritance patterns on allele frequency even without any prior information about the inheritance patterns (i.e., information about inheritance patterns is not provided as an input to the model).

Further, a variant in a gene associated with a disease with higher severity, higher penetrance, and earlier disease onset is conventionally assumed to have a lower calculated probability of pathogenicity than a variant in a gene associated with a disease with lower disease severity, lower penetrance, and later onset, for a given allele frequency. For example, FIG. 8A shows the results of population frequency modeling using the described approach, for two genes (i.e., MLH1, KMT2D) associated with different modes of severity, penetrance, and age of onset. As shown, use of the described approach reveals that the probability of pathogenicity at a given allele frequency can differ greatly between genes that have the same inheritance pattern but different severity, penetrance, and onset.

Figure 8C:
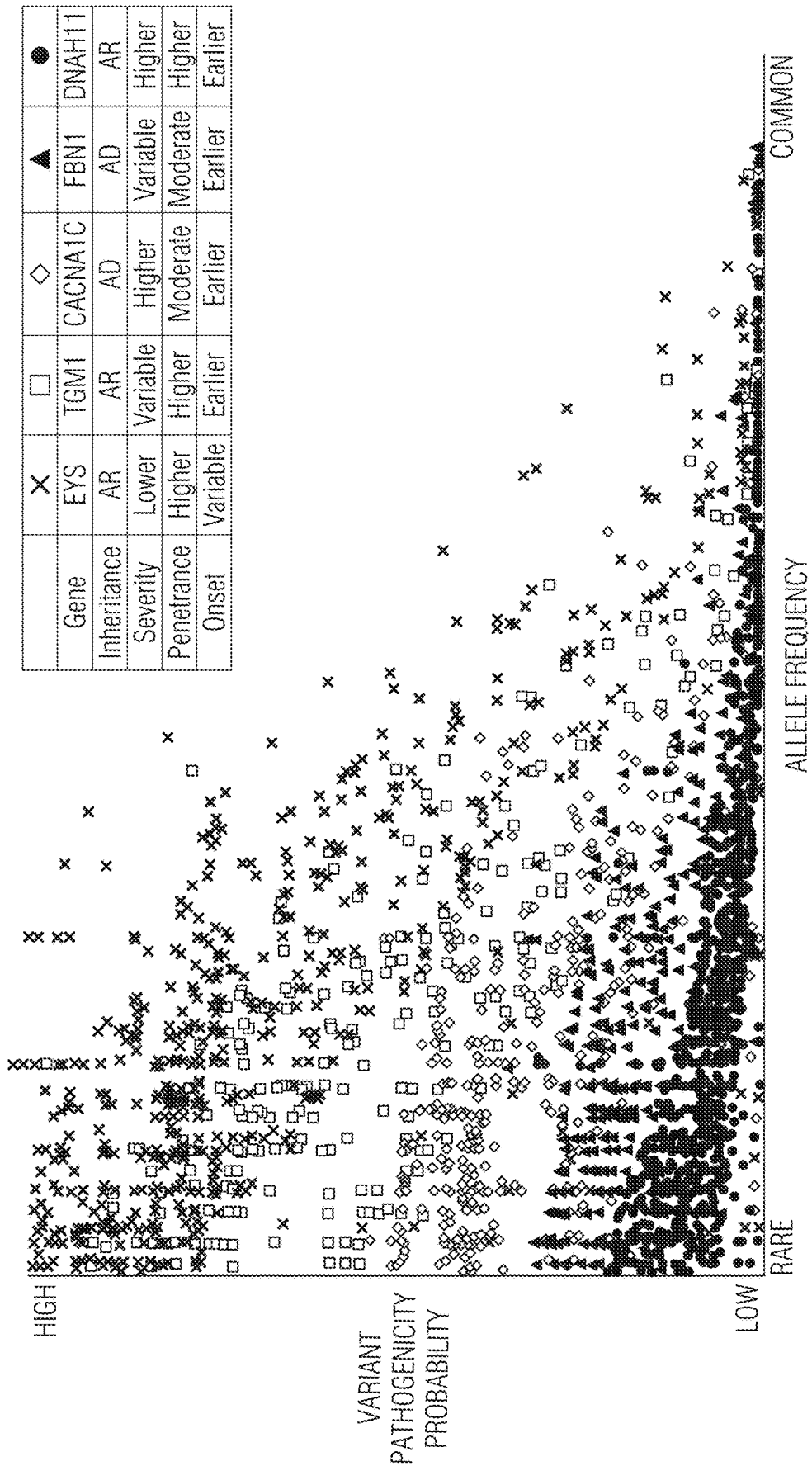
FIG. 8C illustrates another example of population frequency modeling results for a population frequency model configured using a logistic regression model, in accordance with some embodiments of the present disclosure.

Even when comparing multiple genes that have complex combinations of gene-disease attributes, an embodiment of the population frequency model configured as described herein has provided probabilities of variant pathogenicity that fit with the known gene-disease attributes, even though information about those gene-disease attributes is not provided to the model. For example, FIG. 8C shows the results of population frequency modeling for five genes (i.e., EYS, TGM1, CACNA1C, FBN1, DNAH11) associated with different modes of inheritance, severity, penetrance, and age of onset. As shown, use of the described approach reveals that the probability of pathogenicity at a given allele frequency can differ greatly between any two genes, even when both genes are associated with, for example, the same inheritance pattern (e.g., DNAH11 and EYS) or similar penetrance and age of onset (e.g., CACNA1C and FBN1).

In view of the experimental results achieved thus far, a population frequency model configured as described represents a highly accurate, highly scalable, and fully quantitative solution to determining the predictive value of population allele frequencies in the context of individual genes and across genes.

Additionally or alternatively, embodiments of the population frequency model can be used to identify subtle but potentially important biological differences between genes, such as differences observed among DNAH11, DNAI1 and DNAH5.

Incorporation of the described tool into a variant classification framework, such as the Sherloc interpretation system, substantially increases the ability to accurately and confidently classify variants. Within Sherloc, for example, an embodiment of the population frequency model described has been applied to four times as many variants as an earlier method that utilized allele frequencies from gnomAD in an alternative manner, leading to the resolution of approximately 15,000 unique VUS when implemented. Through simulation experiments on historical VUS in a local database, using a process of conservative thresholding of the model output, it is estimated that the described tool will result in an approximately 2.5% reduction in VUS compared with other existing methodologies for assessing population allele frequency data. The reduction in VUS provided by the described model could be further improved in other variant classification frameworks that do not utilize such a conservative thresholding approach.

The disclosure will be understood more fully from the detailed description given below, which references the accompanying drawings. The detailed description of the drawings is for explanation and understanding, and should not be taken to limit the disclosure to the specific embodiments described.

In the drawings and the following description, references may be made to components that have the same name but different reference numbers in different figures. The use of different reference numbers in different figures indicates that the components having the same name can represent the same embodiment or different embodiments of the same component. For example, components with the same name but different reference numbers in different figures can have the same or similar functionality such that a description of one of those components with respect to one drawing can apply to other components with the same name in other drawings, in some embodiments.

Also, in the drawings and the following description, components shown and described in connection with some embodiments can be used with or incorporated into other embodiments. For example, a component illustrated in a certain drawing is not limited to use in connection with the embodiment to which the drawing pertains, but can be used with or incorporated into other embodiments, including embodiments shown in other drawings.

FIG. 1 illustrates an example of a feature generation process for machine learning-based population frequency modeling, in accordance with some embodiments of the present disclosure.

In FIG. 1, a data set of sequence data 110 includes DNA sequence data for one to N human populations, where N is a positive integer and a population can be defined by any one or more demographic criteria. A DNA sample includes one or more genes 102. Each gene includes one or more regions 104, e.g., contiguous groups or sequences of nucleotides or proteins (e.g., A G A C GC T, where A refers to adenine, G refers to guanine, C refers to cytosine, T refers to taurine). Each nucleotide in a region has one or more positions at which variants may be located. For instance, in FIG. 1, person one of population N has cytosine at position 106 of region 104 of their copy of gene 102, while person two of population N has taurine at position 106 of region 104 of their copy of gene 102, where taurine is considered a genomic variant 108.

For each population in the one to N human populations, the sequence data 110 includes gene-level data corresponding to each gene 102, region-level data corresponding to one or more regions 104, position-level data corresponding to one or more positions 106, and variant-level data corresponding to one or more genomic variants 108. Gene-level data refers to any property, attribute, or metric that is determined for a defined sequence of DNA identified as a gene. Region-level data refers to any property, attribute, or metric that is determined for a region of a gene, i.e., a defined portion of a gene that is typically larger than a position but smaller than the entire gene. Position-level data refers to any property, attribute, or metric that is determined for a position within a gene, i.e. a single nucleotide or amino acid position in the gene. Whereas typically, a gene can be thousands of nucleotides long, a variant typically occurs at a single position among those thousands of nucleotides. Region can refer to a portion of a gene that includes a variant and one or more adjacent or neighboring nucleotides.

The gene-level data includes information that is specific to a particular gene, such as gene length. The region-level data includes information that is specific to a particular region of the gene. For example, region-level data can include a property of a region that includes a variant. The position-level data includes information that is specific to a particular position of the gene regardless of whether a variant is present at that position. The variant-level data includes information about a particular variant located at a particular position of the gene. A variant can include more than one nucleotide. When a variant includes more than one nucleotide, the position of the variant refers to a region, such that the terms position and region may be synonymous in that context. A source of sequence data 110 can be a publicly available population database, such as gnomAD.

In FIG. 1, a feature generation process 100 generates a feature set 112 for input to a machine learning model. The feature generation process 100 includes a feature extraction and computation sub-process 114 and a feature transformation sub-process 116. Feature extraction and computation sub-process 114 extracts and/or computes gene-level features 118, variant-level features 120, region-level features 122, and position-level features 124. For example, feature extraction and computation sub-process 114 extracts features from a population database and/or computes the features based on data extracted from the population database. An example of a computed feature is a confidence interval associated with another feature, e.g., a confidence interval computed for an allele frequency.

Feature transformation sub-process 116 applies one or more feature transformations to one or more combinations of gene-level features 118, variant-level features 120, region-level features 122, and/or position-level features 124 to produce population frequency meta-features 126. Feature transformation may refer to an operation that is performed on a computed feature. For example, a computational operation can be applied to a raw feature (e.g., raw observed or measured data) to generate a computed feature, and another computational operation can be applied to a computed feature to perform a feature transformation on the computed future, for example to arrive at a population frequency meta-feature 126.

Examples of feature transformations that can be applied to one or more combinations of gene-level features 118, variant-level features 120, region-level features 122, and/or position-level features 124 to produce population frequency meta-features 126 include mathematical operations such as logarithm, exponent, square root, sum, multiplication, average, mean, median, and/or other mathematical functions. Examples of population frequency meta-features 126 include features that are mathematical combinations of gene-level features and variant-level features or position-level features. For instance, population frequency meta-features quantify the predictive value of allele frequency for a particular variant, region, or position within a gene, within a given population. For example, population frequency meta-features 126 quantify how reliable population allele frequency is as an indicator of pathogenicity for a particular variant, region, or position, within a gene, within a population. Examples of population frequency meta-features 126 include expected frequency distributions of known benign variants and known pathogenic variants within a particular gene within a particular population.

Examples of features that can be included in feature set 112 are shown in Table 1 below. In an embodiment, data from gnomAD (v2.1.1) including ancestry-specific allele counts, allele numbers, and gene-level constraint estimates (e.g., LOEUF) were collected for single nucleotide variants in genes with at least one strong disease association according to a reference genetics knowledge base (e.g., a local, internally-developed knowledge base).

TABLE 1

Examples of Features.

| | |
|---|---|
| Variant-level data | Allele frequency (AF) |
| | Position-level constraint |
| | Moving window missense |
| | Minor allele frequency (MAF) of the variant |

TABLE 1-continued

Examples of Features.

| | |
|---|---|
| | Highest gnomAD ancestry-specific allele frequency (POPMAX) |
| | Confidence intervals around MAF and POPMAX |
| | Identity of POPMAX |
| | Index of fixation (FST) |
| Gene-level data | Gene length |
| | Gene-level constraint (i.e., intolerance of loss-of-function variants, LOEUF, where LOEUF refers to loss-of-function observed/expected upper-bound fraction) |
| | Observed/expected missense variant ratio |
| | Observed/expected synonymous variant ratio |
| | Constraint (LOEUF/pLI, where pLI refers to probability of being loss-of-function intolerant) |
| | Synonymous/nonsynonymous ratio |
| Position- (or region-) level data | Local constraint (i.e., intolerance of loss of function for a region of the gene) |
| Population frequency meta-features | Allele frequency-related feature transformations |
| | Allele frequency relative to constraint |

In an embodiment, features (also referred to as properties) and per-group confidence intervals were generated, yielding feature sets for 33,402 total variants. Some of the features, such as allele frequency, are obtained from a population database such as gnomAD. Other features, such as position-level constraint, are computed based on raw data obtained from the population database. Constraint is a metric that is computed in an external data set released to the public through, for example, gnomAD. Constraint indicates the amount of variation that is tolerated for a gene in the human population. As such, constraint can be used as a signal to identify genes that are more or less constrained; i.e., more or less essential for normal healthy human function. Constraint is a gene-level feature.

Another example of a gene-level feature is synonymous to non-synonymous ratio. Synonymous means that a variant does not result in a change in the protein, and non-synonymous means that the variant would result in a change in the protein. The synonymous to non-synonymous ratio indicates the degree to which non-synonymous variants have been selected against throughout evolution, indicating an intolerance of protein variation for an essential protein function.

Fixation index (FST) is a computed future that indicates allele frequency differentiation between different subpopulations. For example, allele frequency may be obtained from the population database for several different subpopulations (e.g., southeast Asian, African, etc.), and based on the subpopulation allele frequency data, a calculation can be performed that indicates how differentiated the allele frequency is across populations.

Another example of a position-level feature is identity (ID) of max subpopulation, i.e., an ancestry group that has been identified as the highest allele frequency for a particular variant. ID of max subpopulation can be computed by first calculating the allele frequency for the variant for each subpopulation and then ranking or sorting the subpopulations based on allele frequency. Still another example of a position-level feature is actual frequency in the max population, e.g., the x % (e.g., 95%) upper boundary of allele frequency in the identified max subpopulation.

An example of a region-level feature is moving window missense. Moving window missense is the number of missense mutations (a nucleotide mutation that results in a change of amino acid, i.e., a meaningful change in the protein) in a region of a gene. Moving window missense can indicate the degree to which missense mutations are tolerated in a particular region of a gene.

A feature transformation can be applied to the gene-level constraint to apply the constraint information at the variant level. For instance, a mathematical combination (e.g., a log transformation) of allele frequency and constraint is an example of a population frequency meta-feature. Another example of a population frequency meta-feature is position-level constraint. The position-level constraint is created by applying a feature transformation to the gene-level constraint. For example, position-level constraint can be computed by taking the average constraint per position over the gene. Position-level constraint indicates the degree to which a particular position or region within a gene is constrained (as opposed to the overall gene). The position-level constraint can be computed by using variants observed in a region as a normalizing metric against the gene-level constraint. Another example of a population frequency meta-feature is an allele frequency confidence interval to which a feature transformation is applied, for example a binomial proportion of the allele frequency confidence interval.

Another example of a population frequency meta-feature is AF_DIV_LOEUF, which is computed by dividing allele frequency by constraint and then taking the exponent of the resulting quotient. Another example of a population frequency meta-feature is SIN2_MIS_EXP, which is the exponent of the ratio of synonymous to nonsynonymous missense variants in a gene.

Other examples of population frequency meta-features can be created by applying one or more feature transformations to combinations of one or more gene-level features and allele frequency, or to combinations of gene-level constraint and one or more variant-level features and/or position-level features.

Figure 2:
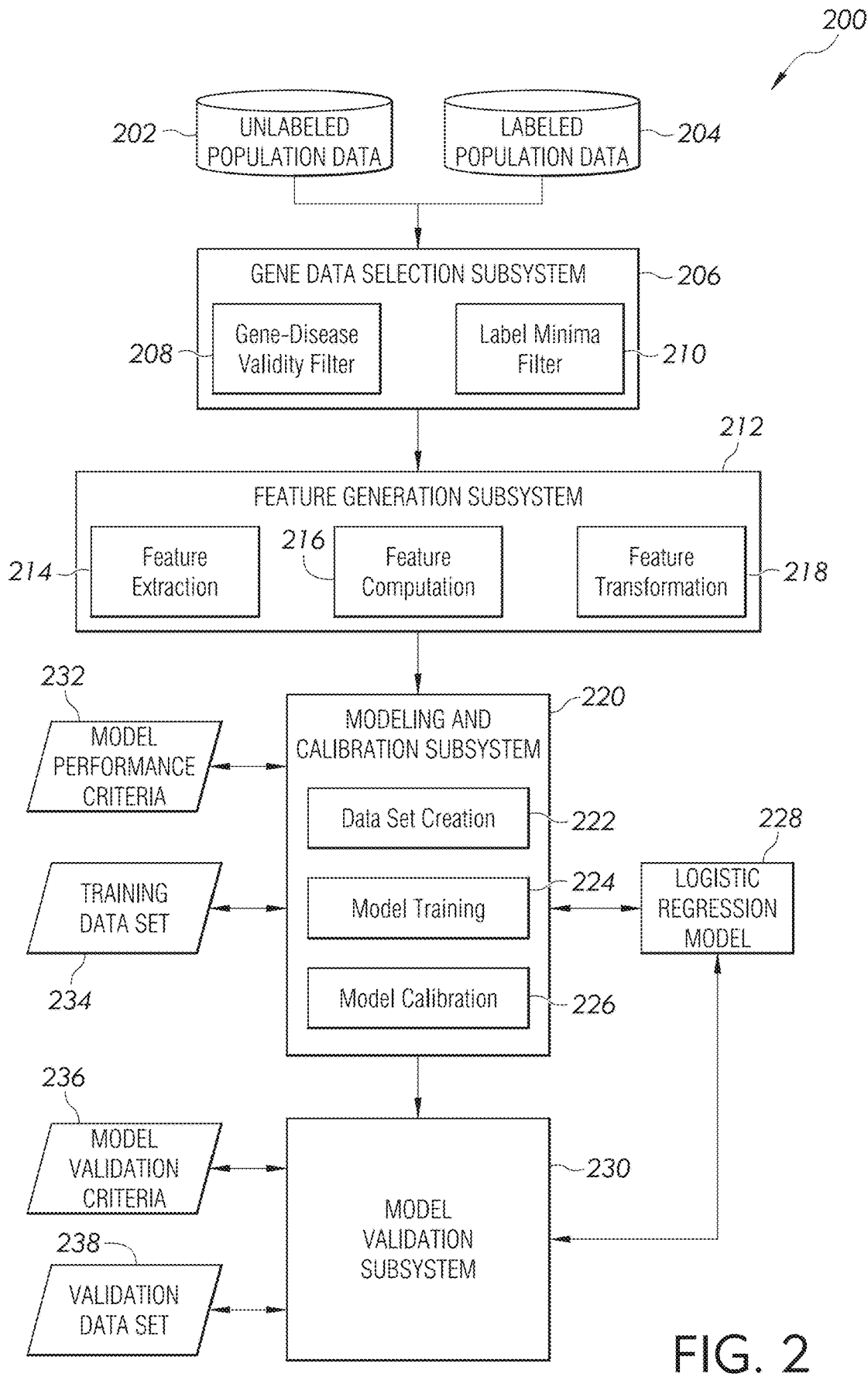
FIG. 2 illustrates an example of a process for configuring a population frequency model using a logistic regression model, in accordance with some embodiments of the present disclosure.

FIG. 2 illustrates an example of a process for configuring a population frequency model using a logistic regression model and machine learning techniques, in accordance with some embodiments of the present disclosure. The process is performed by processing logic that includes hardware (e.g., processing device, circuitry, dedicated logic, programmable logic, microcode, hardware of a device, integrated circuit, etc.), software (e.g., instructions run or executed on a processing device), or a combination thereof. In some embodiments, the method is performed by components of a computing system, including, in some embodiments, components or flows shown in FIG. 2 that may not be specifically shown in other figures and/or including, in some embodiments, components or flows shown in other figures that may not be specifically shown in FIG. 2. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, at least one process can be omitted in various embodiments. Thus, not all processes are required in every embodiment. Other process flows are possible.

In FIG. 2, a model development process 200 prepares one or more data sets, e.g., training data set 234, validation data set 238, for input to a machine learning model, e.g., logistic regression model 228, using one or more machine learning techniques. Portions of the process 200 are performed by components of a population frequency modeling computing system (e.g., population frequency modeling system 1050 of FIG. 10, described below) including a gene data selection subsystem 206, a feature generation subsystem 212, a modeling and calibration subsystem 220, and a model validation subsystem 230. Data sources from which data is received during various portions of the process 200 include unlabeled population data 202, labeled population data 204, logistic regression model 228, model performance criteria 232, training data set 234, model validation criteria 236, and validation data set 238.

Unlabeled population data 202 includes DNA sequence data for one or more human populations. For example, unlabeled population data 202 includes population data extracted from gnomAD or a similar database. The unlabeled population data 202 does not include associated pathogenicity labels or scores. Pathogenicity labels or scores (e.g., benign or pathogenic) are obtained from labeled population data 204. Labeled population data 204 is a reference database that links variants with associated ground-truth pathogenicity labels or scores, such as ClinVar or an internally developed database curated by genetic scientists and/or other genetic experts. The ground-truth labels or scores can be joined or merged with corresponding unlabeled population data 202 (e.g., using a common key value) to produce labeled population data to which logistic regression model 228 can be applied using a supervised machine learning approach.

Labeled population data 204 is joined or merged with unlabeled population data 202 either prior to or subsequent to one or more operations of gene data selection subsystem 206. For example, labeled population data 204 may be joined with unlabeled population data 202 to create one or more training data sets and/or validation data sets subsequent to gene data selection subsystem 206.

Gene data selection subsystem 206 evaluates gene-specific data sets of unlabeled population data 202 and selects one or more gene-specific data sets to be used to generate feature sets that can be input to logistic regression model 228. Gene data selection subsystem 206 applies one or more filters to the population data, which include criteria for determining whether a specific gene's data is to be included or excluded from the model development process. For example, genes that do not have a strong association with any disease may not be eligible for inclusion in the population frequency model.

For example, gene data selection subsystem 206 applies a gene-disease validity filter 208 to the unlabeled population data 202 to create a gene-disease validity filtered subset of unlabeled population data 202, joins or merges the gene-disease validity filtered subset with the labeled population data 204 such that each item of the gene-disease validity filtered subset is matched with a corresponding ground-truth label, and then applies a label minima filter 210 to the labeled gene-disease validity filtered subset of the unlabeled population data 202 to produce and output a labeled gene-disease validity and label minima filtered data set.

Gene-disease validity filter 208 evaluates unlabeled population data 202 to filter out data that is not strongly correlated with a disease. For example, gene-disease validity filter 208 retains unlabeled population data 202 pertaining to variants that have a high probability (e.g., greater than or equal to 90%) of being either benign or pathogenic with respect to a particular disease and filters out unlabeled population data 202 pertaining to variants that have an uncertain probability (e.g., less than 90%) of being either benign or pathogenic with respect to a particular disease. Gene-disease association data can be obtained from a publicly available source such as the Geneticus database.

Label minima filter 210 evaluates the labeled gene-disease validity filtered subset of the unlabeled population data 202 against a label minima threshold value. Label minima filter 210 retains items of the labeled gene-disease validity filtered subset of the unlabeled population data 202 having a number of both pathogenic and benign labels that meets or exceeds the applicable label minima threshold values and filters out items of the labeled gene-disease validity filtered subset of the unlabeled population data 202 having a number of labels that does not meet or exceed the label minima threshold value, i.e., that do not have sufficient benign and pathogenic labels to be useful for model training. For example, gene data sets that do not have at least a minimum number of benign labels are filtered out of the data set.

Feature generation subsystem 212 generates features to be included in a feature set for input to a logistic regression model. For example, embodiments of feature generation subsystem 212 generate various features using the feature extraction, feature computation, and feature transformation techniques described above with reference to FIG. 1.

Feature generation subsystem 212 receives as input the labeled gene-disease validity and label minima filtered data set and generates feature sets (e.g., feature sets 112) based on the received labeled gene-disease validity and label minima filtered data set. Feature generation subsystem 212 includes a feature extraction component 214, a feature computation component 216, and a feature transformation component 218. Feature extraction component 214 extracts features from the received labeled gene-disease validity and label minima filtered data set. The extracted features can include raw features and/or computed features. Examples of raw features and computed features are described above with reference to FIG. 1.

Feature computation component 216 applies one or more computational operations to one or more raw features created by feature extraction component 214. Examples of computational operations that can be applied to one or more raw features are described above with reference to FIG. 1.

Feature transformation component 218 applies one or more computational operations to one or more computed features created by feature extraction component 214 or feature computation component 216. Examples of feature transformations that can be applied to one or more computed features are described above with reference to FIG. 1.

Feature generation subsystem 212 generates and outputs feature sets including raw features, computed features, and/or feature transformations. Examples of features and feature sets that can be generated and output by feature generation subsystem 212 are described above with reference to FIG. 1.

Modeling and calibration subsystem 220 receives as input the feature sets engineered and output by feature generation subsystem 212. Modeling and calibration subsystem 220 includes a data set creation component 222, a model training component 224, and a model calibration component 226.

Data set creation component 222 divides the features sets engineered and output by feature generation subsystem 212 into training and validation data sets, e.g., training data set 234 and validation data set 238. For example, in some embodiments, data set creation component 222 creates gene-specific training and validation data sets for each of up to or more than six hundred different genes, where each gene-specific data set include a set of input features (e.g., feature set 112) associated with a particular variant within a particular gene. As an example, for a given variant, each feature set created by data set creation component 222 includes approximately 24 different variant properties, including allele frequency data extracted from a population database such as gnomAD, associated confidence intervals, and gene length, as well as one or more population frequency meta-features.

Model training component 224 and model calibration component 226 execute a model training process that causes logistic regression model 228 to develop a mathematical representation of the relationships between the input features and the ground truth labels, such that the resulting model can be used to predict the pathogenicity of novel variants (i.e., variants that have not been previously seen by the model) based on the input features associated with those novel variants. The mathematical representation of these relationships can be presented as, for example, a two-dimensional plot of feature values (e.g., variant properties) (x-axis) versus pathogenicity labels (y-axis).

Model training component 224 iteratively applies logistic regression model 228 to training data set 234 and adjusts one or more model parameters and/or feature coefficients until the difference between the predicted model output generated by the logistic regression model 228 and the expected model output evidenced by the ground-truth labels obtained via labeled population data 204 satisfies (e.g., meets or exceeds) model performance criteria 232. When the model performance criteria 232 are satisfied, modeling and calibration subsystem 220 ends the model training process and produces the trained logistic regression model 228. A more detailed example of a model training and calibration process that can be used to create the trained logistic regression model 228 is described below with reference to FIG. 4, FIG. 5A, and FIG. 5B.

Model validation subsystem 230 applies a model validation process to the trained logistic regression model 228 produced by modeling and calibration subsystem 220. Model validation subsystem 230 applies the trained logistic regression model 228 to validation data set 238 to determine whether model validation criteria 236 are satisfied (e.g., met or exceeded). A more detailed example of a model validation process is described below with reference to FIG. 6, FIG. 7A, and FIG. 7B.

If the trained logistic regression model 228 is successfully validated by model validation subsystem 230, the validated logistic regression model 228 can be used for inferencing, e.g., to generate pathogenicity predictions or estimates for novel (i.e., previously unseen) variants. Alternatively or in addition, the predictions output by the validated logistic regression model 228 can be stored for future use (e.g., for access or lookup by one or more downstream processes, systems, or services). A more detailed example of a logistic regression model and an inference-time use of a logistic regression model configured for variant classification using the feature sets and techniques described herein is described below with reference to FIG. 3.

Figure 3:
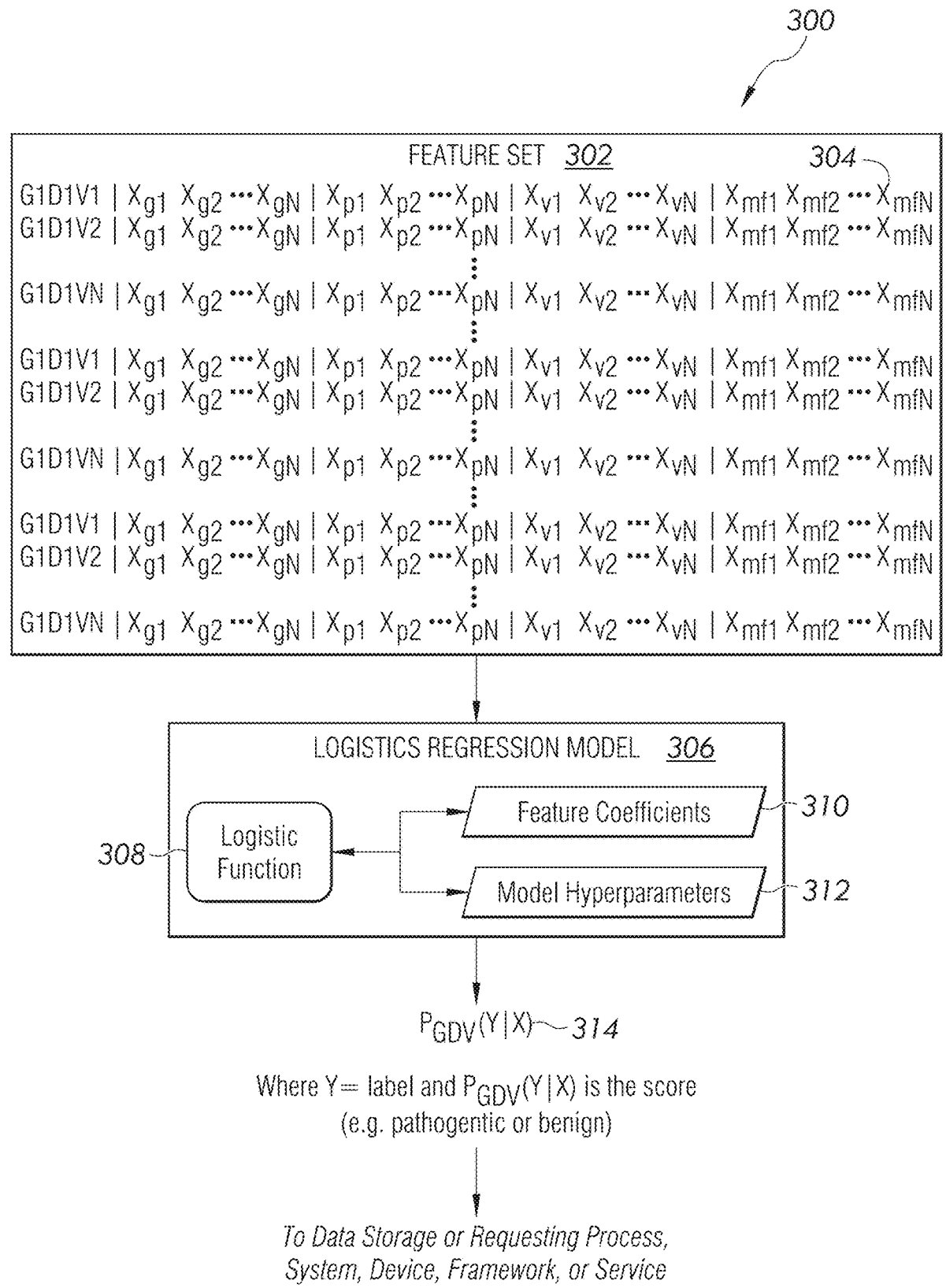
FIG. 3 illustrates an example use of a population frequency model configured using a logistic regression model, in accordance with some embodiments of the present disclosure.

FIG. 3 illustrates an example use of a population frequency model configured using a logistic regression model, in accordance with some embodiments of the present disclosure.

A logistic regression model 306 is a statistical machine learning model that uses the logistic function to model the relationship between X and Y, where the probability of Y is a linear combination of the independent variables in the input X. Mathematically, a simplified $$P(X) = f(x) = \frac{1}{1 + e^{-(\beta_0 + \beta_1 x)}},$$

form of the logistic function can be expressed as where e is the exponential constant and $\beta_0$ and $\beta_1$ are feature coefficients. During training of the logistic regression model 306, logistic regression estimates the values of the coefficients in the linear combination based on the feature values in the training data set.

In FIG. 3, logistic regression model 306 has been configured via supervised machine learning training, calibration, and validation processes described. The logistic regression model 306 includes a logistic function 308. The logistic function 308 includes feature coefficients 310. The feature coefficients 310 include a regression coefficient β for each feature input x (e.g., $f(i)=\beta_0+\beta_1 x_{1,i}+ \ldots \beta_m x_{m,i}$), where i is a particular item of the feature set (e.g., item or row 304) and m is the number of feature inputs x in the feature set 302. The regression coefficient indicates the relative effect of the particular feature input x of the feature set 302 on the predicted outcome P (Y|X), e.g., a predicted pathogenicity label or score, based on the values of the feature inputs x in the feature set 302. The values of the feature coefficients are initialized and adjusted during model training and calibration.

The logistic regression model 306 also includes model hyperparameters 312, which are selected or tuned at a global level and generally are not modified based on specific instances of training data. The model hyperparameters 312 include, for the logistic regression model 306, the penalty or regularization parameter (e.g., L1 or L2) and the C or regularization strength parameter. The penalty or regularization parameter is tunable to adjust model generalization error and regulate overfitting. Typical values of the penalty or regularization parameter are L1 and L2. In some embodiments of logistic regression model 306, the penalty or regularization parameter is set to L1. The C or regularization strength parameter regulates overfitting in conjunction with the penalty. Smaller values of C specify stronger regularization. Regularization imposes a cost to the complexity of the model by penalizing large coefficient values. Regularization restricts the number of different ways the model can fit the data. The value of C is subject to a hyperparameter optimization process such as grid search. In some embodiments of logistic regression model 306, the value of C is set to a value in the range of about 1 to about 10.

The model hyperparameters 312 can be tuned using, for example, a grid search cross validation procedure. For instance, an automated hyperparameter tuning tool, e.g., GridSearchCV, is used for hyperparameter tuning in some embodiments. In other embodiments, other hyperparameter optimization methods are used, such as random search and Bayesian search. In the illustrated embodiments, hyperparameter tuning was performed over the training data set to compare the performance of various combinations of model types and hyperparameters. The simplest model with the strongest regularization (e.g., an L1-regularized logistic regression model, C=10) that yielded high validation performance (e.g., AUROCvalidation=0.92) was selected for inferencing. Model predictions for the training and validation data sets were separately generated by averaging the calibrated predictions from ten-fold cross validation such that the validation data set was not used for training set predictions. Inference over VUS was performed by first refitting the model to the entire labeled set prior to predicting on the new variants.

The logistic regression model 306 can be configured either as a binary classifier or as a scoring model. In a binary classification mode, the output of the logistic regression model 306 indicates whether the predicted outcome is pathogenic or benign as a binary value, e.g., zero indicates benign and one indicates pathogenic, for a given set of input features. In a scoring mode, the output of the logistic regression model 306 includes a score, which corresponds to a probability that the predicted outcome is pathogenic or benign (e.g., a numerical value between zero and 1, inclusive).

The logistic regression model 306 can be configured and implemented as a network service. For example, the logistic regression model 306 can be configured using a machine learning library such as scikit-learn. For example, the logistic regression model 306 can be configured via an application programming interface (API), e.g., via an API call such as ML_library.model.logistic_regression(p1, p2, . . . pn), where p indicates a parameter or argument of the call, such as a model hyperparameter or an input feature set identifier. Once configured, the logistic regression model 306 and/or its output can be hosted on one or more servers and/or data storage devices for accessibility to one or more requesting processes, systems, devices, frameworks, or services.

In FIG. 3, feature set 302 includes an item or instance of features 304 for each gene-disease-variant combination. For example, feature set 302 includes an item or instance of features 304 for N genes, N diseases, and N variants, where the value of N may be the same or different in each case. Each item or instance 304 includes one or more gene-level features $x_{g1} \ldots xg_N$, one or more position-level features $x_{p1} \ldots x_{pN}$, one or more variant-level features $x_{v1} \ldots x_{vN}$, and one or more population frequency meta-features $x_{mf1} \ldots x_{mfN}$. Examples of gene-level features $x_{g1} \ldots xg_N$, position-level features $x_{p1} \ldots x_{pN}$, variant-level features $x_{v1} \ldots x_{vN}$, and population frequency meta-features $x_{mf1} \ldots x_{mfN}$ include those described with reference to FIG. 1. Alternatively or in addition, feature set 302 can include region-level features. In other embodiments, feature set 302 may include gene-level features, variant-level features, and population frequency meta-features but not include position-level features or region-level features. Features 304 can be grouped into a feature set 302 using, for example, a concatenation function.

Embodiments of the features set 302 are limited to numerical features and categorical features that are quantitative, and do not include qualitative features or gene-disease attributes. Prior to input to logistic regression model 306, an item or instance of features 304 can be converted to a vector representation. In some embodiments, the vector representation of the features is converted to a compressed form such as an embedding, prior to input to logistic regression model 306.

In response to each instance of features of feature set 302, logistic regression model 306 computes and outputs an estimated outcome $P_{GDV}(Y|X)$ 314. The estimated outcome produced by logistic regression model 306 based on an instance of features of feature set 302 is in the form of a binary output (e.g., zero for benign or one for pathogenic) or a score (e.g., a value between zero and one. The output can be stored in a data storage for subsequent lookup or provided to one or more downstream systems, processes, devices, frameworks, and/or services.

Figure 4:
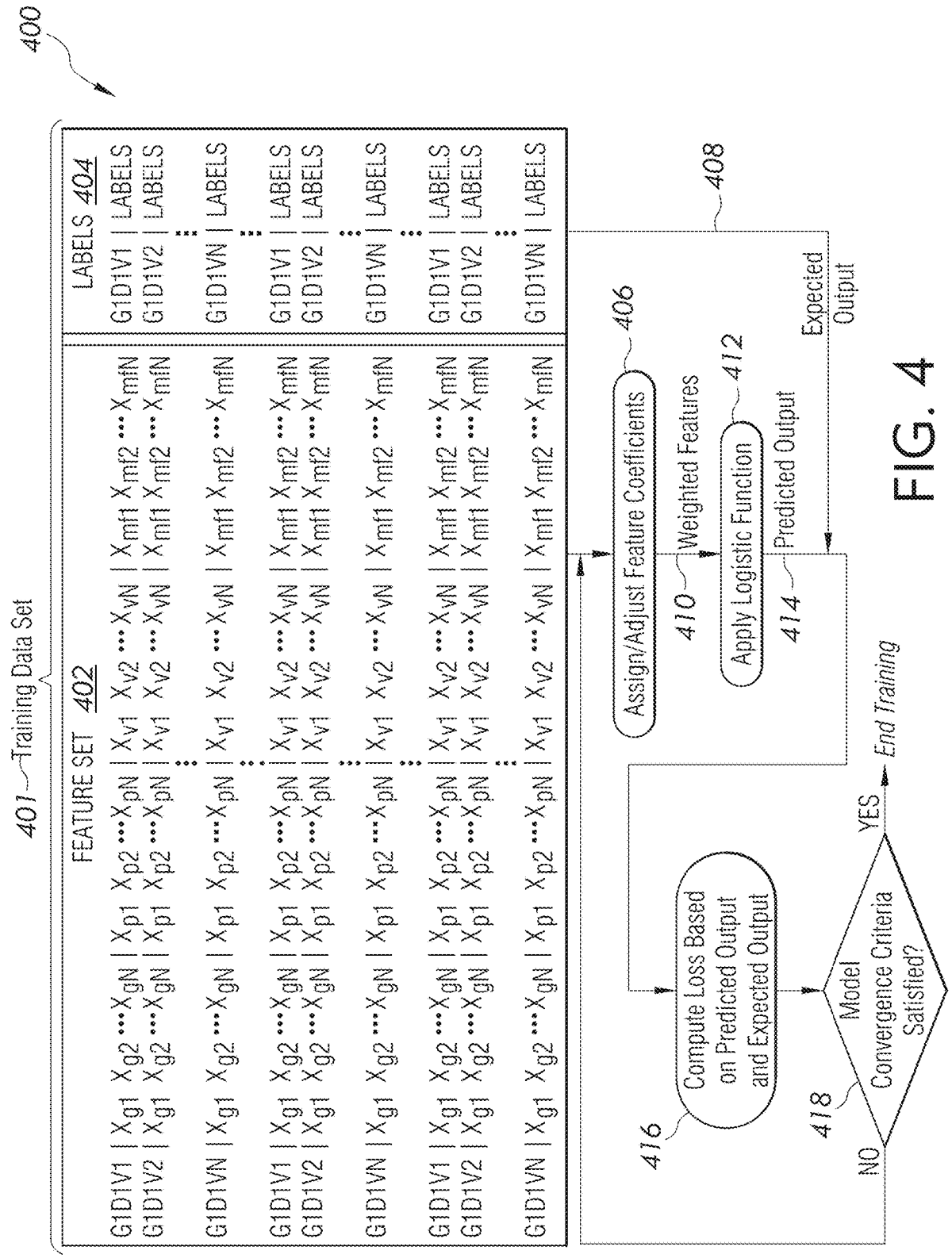
FIG. 4 illustrates an example process for configuring a population frequency model using a logistic regression model, in accordance with some embodiments of the present disclosure.

FIG. 4 illustrates an example process for configuring a population frequency model using a logistic regression model, in accordance with some embodiments of the present disclosure. In FIG. 4, a model training process 400 applies a logistic function to a training data set 401 using regression-based supervised machine learning. The training data set 401 includes feature set 402 and labels 404. Feature set 402 is similar to feature set 302, with ground-truth labels appended to each corresponding item or instance of the feature set as described. In an embodiment, feature sets for 33,402 total variants (i.e., labels) were used for training across 823 genes (n=18,148 benign and 15,234 pathogenic variants). All training variants from 25% of genes were set aside, as a test (or validation) set, and remained unused until after the completion of model training. Exclusion of labeled training data based on a selection of genes is not required; i.e., not all embodiments are required to hold out training sets in the described way.

On a first training iteration, feature coefficients are initialized or assigned to each feature input of the feature set 402, at sub-process 406. Feature coefficients are initialized by setting the coefficient values randomly, for example. The feature coefficient values assigned at sub-process 406 operate as weights that are applied to the respective features to produce weighted features 410. The logistic function is applied to the weighted features at sub-process 412 to produce predicted output 414. The ground truth labels 404 provide the expected output 408 for supervised machine learning. The predicted output 414 is evaluated by computing a loss (or error) based on the expected output 408 and the predicted output 414, at sub-process 416. The loss is computed using a loss function, such as a gradient descent algorithm.

On each iteration, the decision sub-process 418 evaluates the difference between the predicted output and the expected output, for example using a comparison of output of the loss function against a stopping condition that depends on the change in the output of the loss function. The change in the output of the loss function is compared to an error tolerance threshold (which may be referred to herein as a model performance criterion or model convergence criterion). If the model performance criteria, e.g., error tolerance threshold, is not satisfied (e.g., not greater than or equal to a threshold performance level, or exceeds a maximum permitted error value, or the loss has not stopped improving by more than the tolerance, or the error has not stopped decreasing by more than the tolerance threshold), the model training continues for another iteration. If the loss has stopped improving by more than the tolerance threshold, then the model has converged and the training ends.

On subsequent training iterations, the values of one or more of the feature coefficients are adjusted, the logistic function is applied to additional instances of the feature set 402, and the output of the logistic function is evaluated using the loss function and error tolerance as described above. The training process 400 ends when the model performance criteria, i.e., the error tolerance threshold, is satisfied and the model converges (e.g., the output of the comparison, e.g., loss function, is greater than or equal to a threshold performance level, or is within or below the maximum permitted error value, or the loss has stopped improving by more than the tolerance threshold).

Figure 5A:
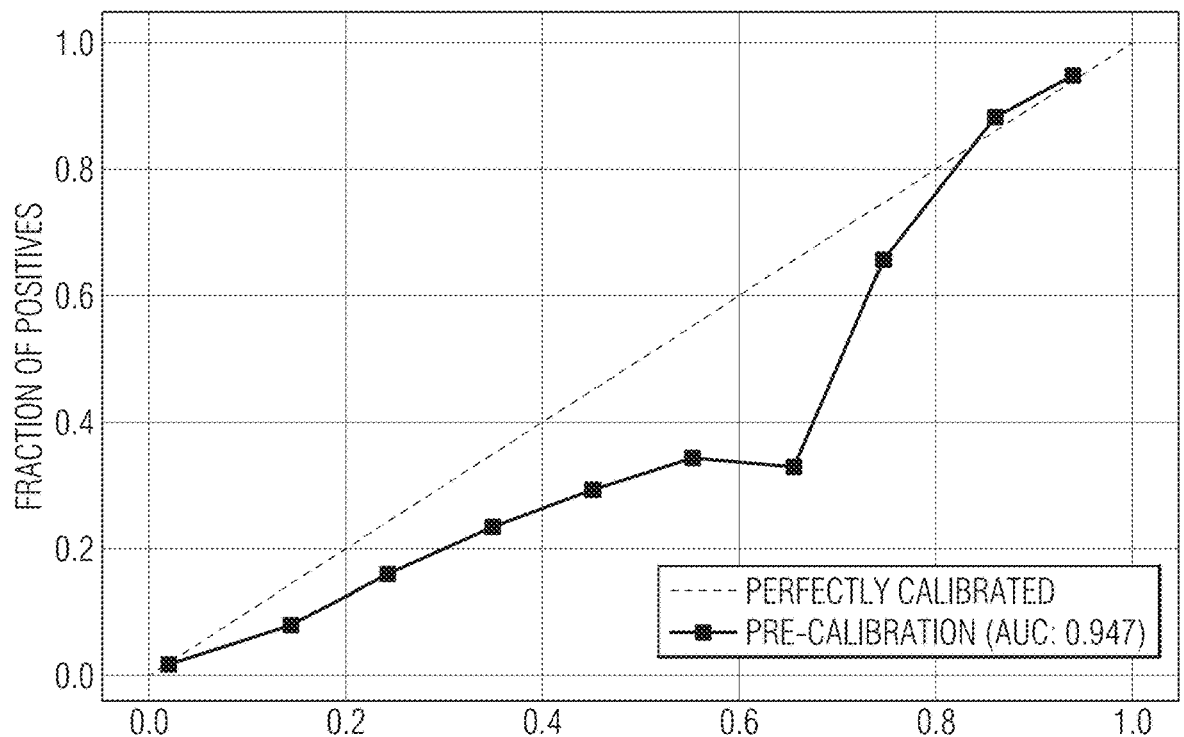
FIG. 5A illustrates an example of a pre-calibration curve for a population frequency model configured using a logistic regression model, in accordance with some embodiments of the present disclosure.

FIG. 5A illustrates an example of a pre-calibration curve for a population frequency model configured using a logistic regression model, in accordance with some embodiments of the present disclosure.

In operation, for a given gene, variant, and disease, an embodiment of the population frequency model typically outputs a large number of scores that are close to zero (e.g., benign) and also a large number of scores that are close to one (e.g., pathogenic). FIG. 5A shows an example of a pre-calibration curve in comparison to the desired or perfect calibration. Before calibration, the model tends to underestimate the variant pathogenicity probability in the lower score region (e.g., the portion of the pre-calibration curve below the perfect calibration line). The difference between the perfect calibration and the pre-calibration curve may be referred to as the error. The calibration process adjusts the values on the pre-calibration curve so that they more closely align with the perfect calibration diagonal. Depending on the error for a given region of the model output, the score is shifted (e.g., by adjusting one or more model coefficients) so that expected probability matches the predicted probability. The pre-calibration curve of FIG. 5A is an aggregate curve of scores output by the model for multiple different genes. A similar calibration process can be performed using similar curves for individual genes.

Figure 5B:
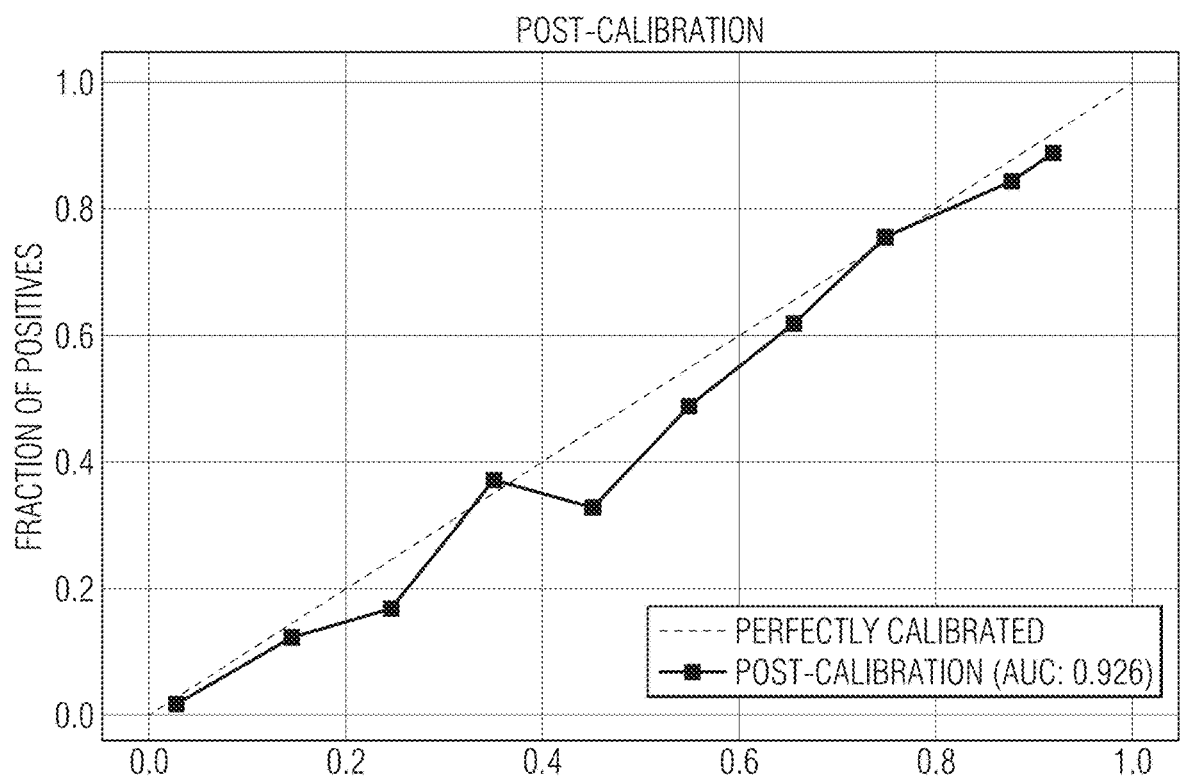
FIG. 5B illustrates an example of a post-calibration curve for a population frequency model configured using a logistic regression model, in accordance with some embodiments of the present disclosure.

FIG. 5B illustrates an example of a post-calibration curve for a population frequency model configured using a logistic regression model, in accordance with some embodiments of the present disclosure. FIG. 5B shows an example of a post-calibration curve in comparison to the desired or perfect calibration, resulting from calibration applied to the curve of FIG. 5A. After calibration, the model output tends to align more closely with the perfect calibration line. The post-calibration curve of FIG. 5B is an aggregate curve of scores output by the model for multiple different genes. A similar calibration process can be performed using similar curves for individual genes.

Figure 6:
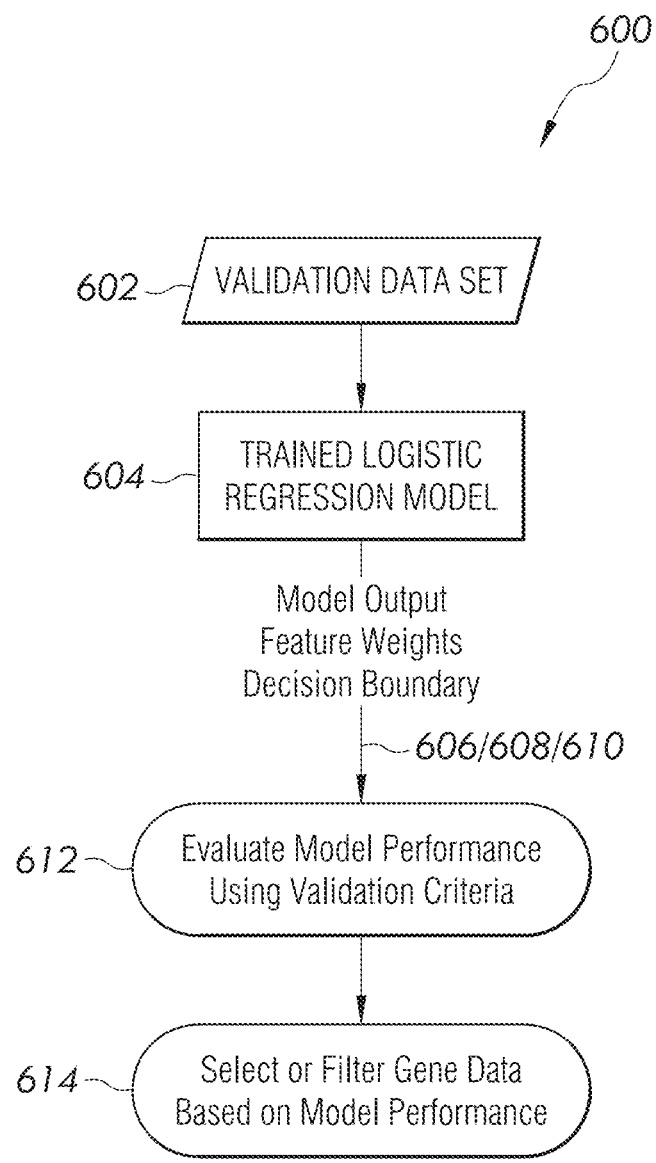
FIG. 6 illustrates an example of a process for validating a population frequency model configured using a logistic regression model, in accordance with some embodiments of the present disclosure.

FIG. 6 illustrates an example of a process for validating a population frequency model configured using a logistic regression model, in accordance with some embodiments of the present disclosure. In FIG. 6, a validation process 600 applies a trained logistic regression model 604 to a validation data set 602. An example of a validation data set 602 is a portion of feature set 402 that has been set aside for validation and not used for training. For example, referring to FIG. 2, data set creation component 222 creates several gene-specific splits of the data and holds out specific data sets for entire genes, which are not used for model training but can be used to create validation data sets. The trained logistic regression model 604 is, for example, a logistic regression model trained and configured as described herein.

Responsive to the processing of the validation data set 602, the trained logistic regression model 604 provides validation parameters such as model output 606, feature weights 608, and decision boundary 610 to a sub-process 612 for evaluation. Sub-process 612 evaluates the performance of the trained logistic regression model 604 using validation criteria, e.g., by inspecting samples of the actual model output 606, feature weights 608, and/or decision boundary 610 and comparing the inspected samples to expected or reference values, or by computing one or more validation metrics.

Model validation can be performed over many iterations, with each iteration using a slightly different validation data set that was not used in training. The trained logistic regression model 604 generates pathogenicity predictions over the validation set, and based on the average performance of the model over those splits, the performance of the model parameters can be validated and adjusted. Examples of metrics that can be used to evaluate the model performance include means square error or the area under the receiver operating characteristic curve.

Approaches that can be used to validate the trained logistic regression model 604 include: evaluation of data set performance metrics, decision boundary inspection, evaluation of model-level performance metrics, gene- and variant-level inspection, feature weight inspection, and benchmark comparison to an existing framework (e.g., Sherloc).

Figure 7A:
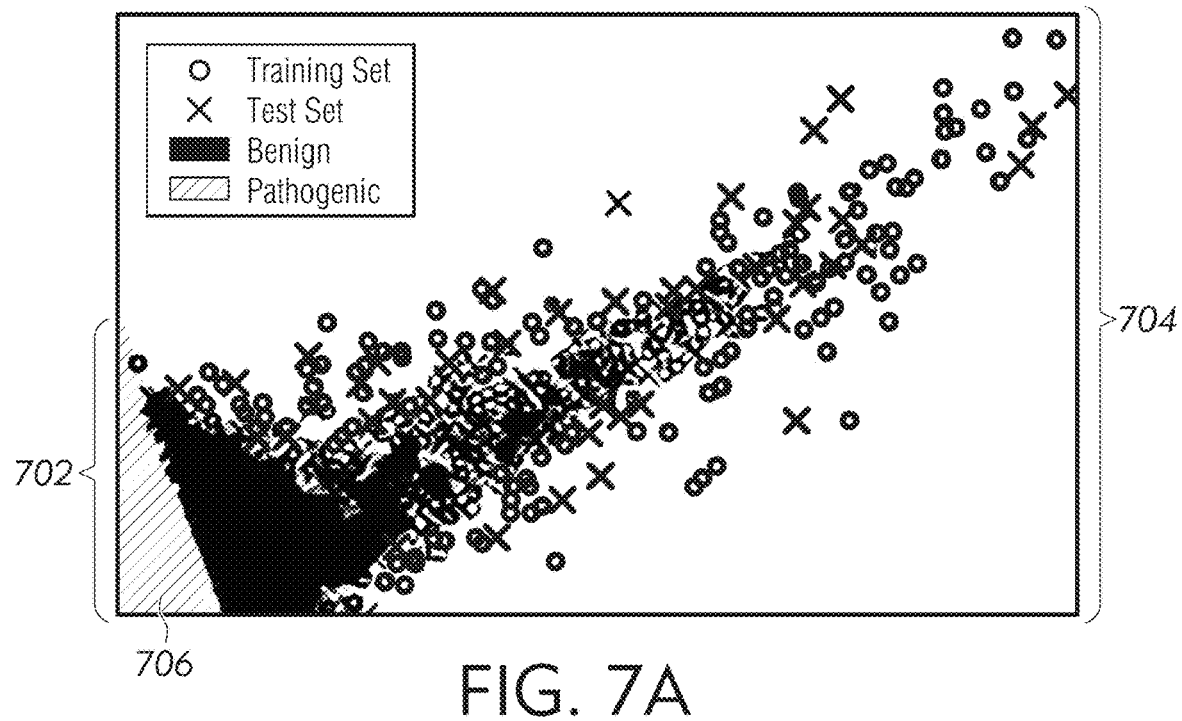
FIG. 7A illustrates an example of a decision boundary for a population frequency model configured using a logistic regression model, in accordance with some embodiments of the present disclosure.
Figure 7B:
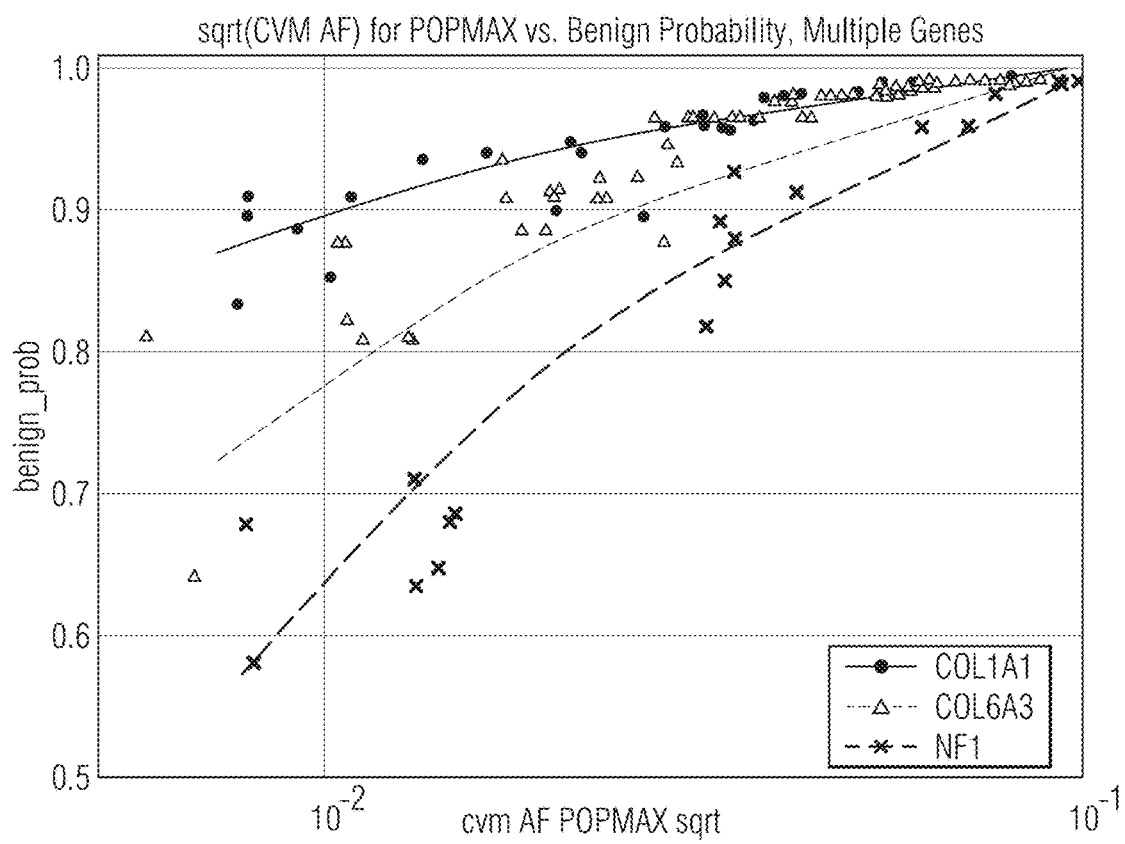
FIG. 7B illustrates an example of gene-specific response curves for a population frequency model configured using a logistic regression model, in accordance with some embodiments of the present disclosure.

Decision boundary inspection refers to a process of evaluating the actual boundary of the model, that is the threshold at which the model distinguishes between benign and pathogenic. An example of an evaluation of a decision boundary is shown in FIG. 7A, described below. An example of an evaluation of a data set performance metric is shown in FIG. 7B, described below.

Responsive to the evaluation of the model performance performed by sub-process 612, certain gene-specific data sets and corresponding model outputs may be selected for inclusion in a database or downstream system, device, process, or service, if the data sets satisfy the respective validation criteria. Alternatively, if a certain gene-specific data set does not satisfy the respective validation criteria, that data set may be excluded or marked as unavailable for subsequent use, e.g., not stored in the database and not provided to any downstream system, device, process, or service.

For technical validation, model outputs were validated at the gene level for performance and calibration. Genes that demonstrated poor calibration (i.e., Brier score>0.15) or poor discrimination performance (i.e., AUROC<0.80) were flagged for exclusion from the final model output. In total, 591 of the original 823 genes achieved sufficiently high calibration and discrimination performance requirements. Of note, the 232 genes flagged for exclusion were nonetheless used for the subsequent step when we calculated performance so as not to artificially bias the overall performance assessment.

For clinical validation, to gain further confidence in the prediction outputs of the population frequency model, a concordance analysis was performed against three internally-developed, independent in silico algorithms that rely on orthogonal data types. In all three comparisons, the concordance rates were high, as shown in Table 2 below.

TABLE 2

Example of Concordance Rates.
Population frequency model benign prediction (≥95% confidence) concordance with non-population in silico models

| Predicted benign (≥95% confidence) | Predicted pathogenic (≥95% confidence) | Concordance rate |
|---|---|---|
| First independent algorithm | | |
| 13,208 | 1,594 | 89.2% |
| Second independent algorithm | | |
| 8,094 | 413 | 95.1% |
| Third independent algorithm | | |
| 33,874 | 2,158 | 94.0% |

Further, model outputs were reviewed for a particularly challenging class of variants: high allele frequency pathogenic variants. These are variants that by population allele frequency data alone resemble benign variants but are classified as pathogenic or likely pathogenic due to other evidence supporting pathogenicity. These include such variants as ancestry-specific founder variants, and hypomorphic alleles associated with milder phenotypes or reduced penetrance relative to typical pathogenic variants in the same gene.

Among the 591 genes included in the analysis, 30 high allele frequency pathogenic variants in 26 genes were identified that would have been classified as benign or likely benign based on allele frequency alone, but had contradictory evidence supporting pathogenicity. Although the population frequency model still predicted 18 of these 30 variants to be strong or moderate benign (NPV>95%), the remaining 12 variants were predicted to be supporting benign (95%>NPV≥80%), supporting pathogenic (PPV≥80%), or insufficiently certain (NPV<80% and PPV<80%). These results indicate that the population frequency model has greater specificity for identifying benign variants than traditional approaches, notwithstanding the fact that critical review of all contradictory evidence is still a necessary part of variant classification. An example of how the NPV/PPV values obtained from the population frequency model as described can be converted to discrete scores, e.g., Sherloc scores (such as 5 benign, 3 benign, 1 benign and 1 pathogenic points) is shown in FIG. 7C, described below.

FIG. 7A illustrates an example of a decision boundary for a population frequency model configured using a logistic regression model, in accordance with some embodiments of the present disclosure. In FIG. 7A, variants are projected onto a two-dimensional plane. The plot of FIG. 7A is a two-dimensional representation of variants represented as circles and x's. To perform decision boundary inspection, one or more points in the plot of FIG. 7A can be sampled and inspected to determine whether the prediction for that variant would be pathogenic or benign. The decision boundary 706 divides points in region 702 (pathogenic) from points in region 704 (benign). Points that are closer to the decision boundary 70 have less certainty as to the associated prediction, while points farther from the decision boundary 706 are more confident classifications.

FIG. 7B illustrates an example of gene-specific response curves for a population frequency model configured using a logistic regression model, in accordance with some embodiments of the present disclosure. Using FIG. 7B, the predictive value of the POPMAX feature can be evaluated for individual genes. The feature on the x-axis is the square root of the computed allele frequency. Increasing allele frequency correlates with increasingly benign predictions. FIG. 7B illustrates that the relationship between allele frequency and benign predictions is different for different genes.

Figure 7C:
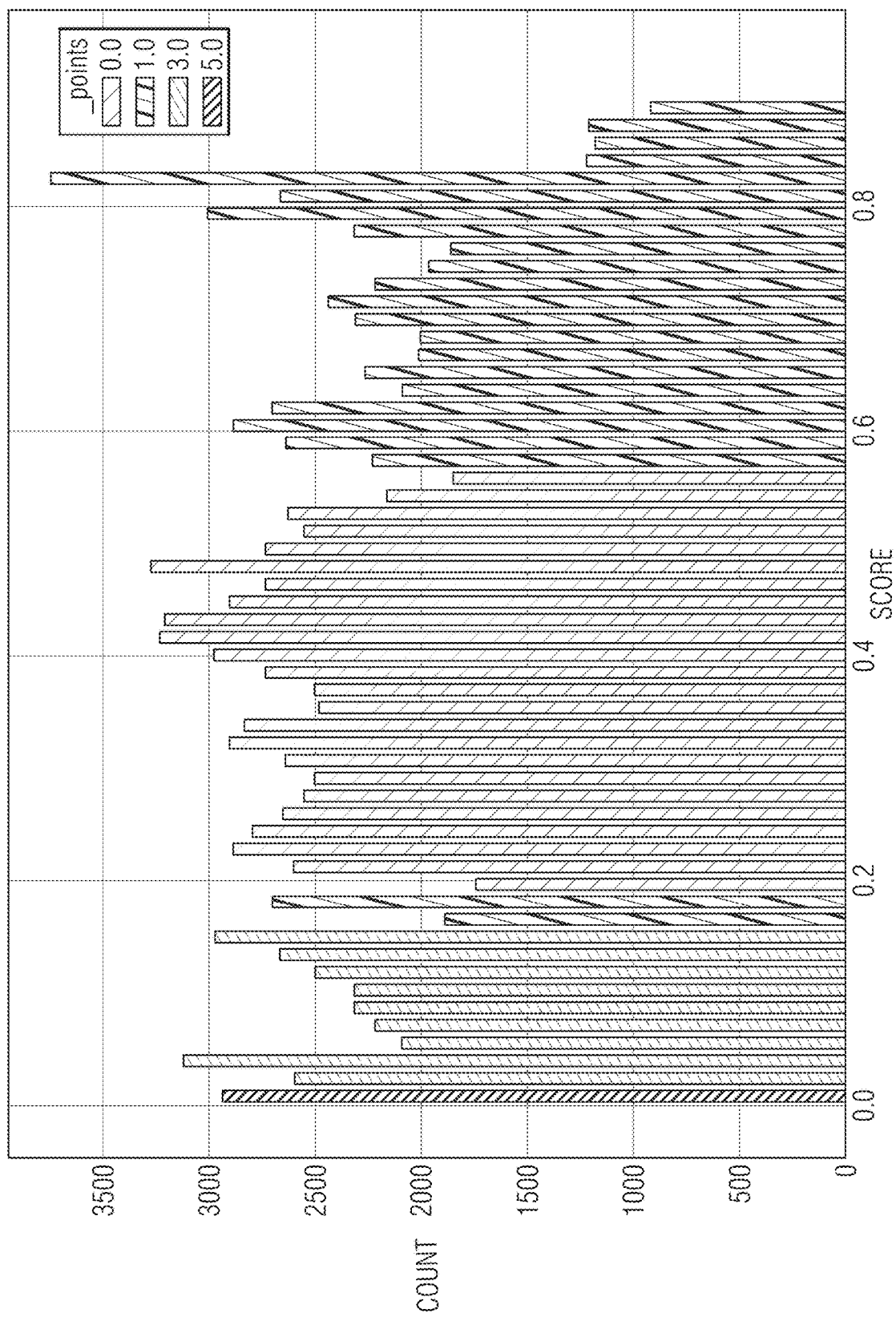
FIG. 7C illustrates an example of variant classification based on a population frequency model configured using a logistic regression model, in accordance with some embodiments of the present disclosure.

FIG. 7C illustrates an example of variant classification based on a population frequency model configured using a logistic regression model, in accordance with some embodiments of the present disclosure. In FIG. 7C, the count of the number of variants having each score value is represented as a histogram. For example, approximately 2900 variants were given a score of zero by the model and more than 3000 variants were given a score greater than 0.8 by the model. The histogram is divided into classification groupings or bins and a point value as associated with each grouping or bin of scores. For example, the portion of the histogram associated with a score of zero is assigned five points (e.g., benign), and the portion of the histogram adjacent the zero-score region is assigned three points (e.g., likely benign), while the portion of the histogram associated with a score greater than 0.6 is associated with a point value of 1. Portions in the middle of the histogram are assigned a point value of zero because the associated score value has lower confidence. The point values assigned based on the model output can be combined with other evidence to which the classification framework is applied.

In general, the number of points associated with a particular score correlates with the confidence or certainty of the prediction. The number of bins does not need to be four; any number of bins (including no bins or an infinite number of bins) can be used. The points that are mapped to the scores output by the model can be incorporated into another variant classification framework such as Sherloc. In this way, output of the population frequency model as described can be applied to the Sherloc framework or to any other variant labeling or classification framework.

To integrate the model predictions into the Sherloc variant classification framework, five tiers of predictions were established based on predictive performance thresholds, as measured in negative predictive value (NPV) and positive predictive value (PPV). Four of these tiers mirrored the existing Sherloc framework for assessing population frequency data and were defined as (1) [strong benign] sufficient confidence to classify as benign, in the absence of compelling contradictory evidence, (2) [moderate benign] sufficient confidence to classify as likely benign, in the absence of compelling contradictory evidence; (3) [supporting benign] consistent with a benign classification, but insufficient to reach a likely benign classification without orthogonal evidence also supporting benignity; and (4) [supporting pathogenic] consistent with a pathogenic classification, but insufficient to reach a likely pathogenic classification without orthogonal evidence also supporting pathogenicity. The predictive performance thresholds for those four tiers were respectively defined as (1) [strong benign]>99% NPV, (2) [moderate benign]>95% to 99% NPV, (3) [supporting benign]>80% to 95% NPV, and (4) [supporting pathogenic]>80% PPV. The fifth and final tier corresponded to predictions below 80% PPV and below 80% NPV, which were deemed insufficiently certain to be assigned a weight within the Sherloc scoring system. The overall model performance as well as tier-level classification performance were assessed over the 25% of genes reserved as a test set. The overall model performance achieved AUROCtest=0.92, confirming that the model generated from the training set generalizes to the test set genes. For the four PPV and NPV tiers, predictive values matched or exceeded the targeted performance over the test set. In the model's current iteration, model outputs were limited to missense and single nucleotide substitution nonsense variants. Future development of the model may extend the scope of its predictions to new variant types.

FIG. 8A, FIG. 8B, FIG. 8C, and FIG. 8D illustrate predictive output, i.e., population frequency modeling results, produced by embodiments of the population frequency model configured as described. FIG. 8A shows a comparison of variants found in the genes MLH1 (associated with Lynch syndrome) and KMT2D (associated with Kabuki syndrome). FIG. 8B shows a comparison of variants found in the genes TSC2 (associated with tuberous sclerosis complex) and LAMA2 (associated with LAMA2-related muscular dystrophy). FIG. 8C shows a comparison of the genes EYS (associated with retinosis pigmentosa), TGM1 (associated with ichthyosis), CACNA1C (associated with epileptic encephalopathy, others), FBN1 (associated with Marfan syndrome, others), and DNAH11 (associated with primary ciliary dyskinesia).

All variants are plotted based on the output produced by embodiments of the population frequency model as described. Each variant (represented as a dot in each plot) is placed along the x-axis according to the allele frequency as reported in the gnomAD population database. The y-axis represents the probability that a variant is pathogenic based on the population frequency model configured as described. Gene-disease attributes for each gene are summarized in the tables, where AD indicates autosomal dominant and AR indicates autosomal recessive.

These model output illuminate the limitations of conventional approaches that draw discrete allele frequency thresholds for variant classification and then applying them broadly to many genes, as has traditionally been done. When such conventional approaches are used, variants can cross a threshold at very different probabilities of pathogenicity, depending on the gene. Of note, variants in DNAH11, associated with autosomal recessive primary ciliary dyskinesia, generally have lower probabilities of pathogenicity than variants with similar allele frequencies in CACNA1C and FNB1, both associated with autosomal dominant conditions. This is possibly due to DNAH11 being associated with a highly penetrant, early-onset, severe, and rare condition, but also likely due to this large gene (4,516 codons) resulting in many different but individually rare pathogenic variants. This further highlights the challenges associated with applying general allele frequency thresholds to many genes.

While the plots of FIG. 8A, FIG. 8B, FIG. 8C, and FIG. 8D illustrate the machine-learned relationships between variant pathogenicity probability and allele frequency for particular genes and variants produced by the population frequency model, it should be understood that the model inputs included other features in addition to allele frequency.

FIG. 8A illustrates an example of population frequency modeling results for a population frequency model configured using a logistic regression model, in accordance with some embodiments of the present disclosure. FIG. 8A shows examples of pathogenicity probabilities that have been estimated and output by the described population frequency model for each variant in two different genes, MLH1 and KMT2D). In FIG. 8A, each dot in the plot represents a different particular variant within a particular gene. The majority of the variants in the gene MLH1 are plotted in region 802 while the majority of the variants in the gene KMT21) are plotted in region 804. The y axis shows the model output, i.e., the probability of pathogenicity for the variant, and the x axis shows the allele frequency for the variant in a given human population. As the frequency of the variant in the population increases, the probability of pathogenicity decreases.

More specifically, FIG. 8A illustrates an example of the population frequency model configured as described outputting variant pathogenicity probabilities that account for differences in genes with the same inheritance pattern. For example, as shown in the table included in FIG. 8A, both MLH1 and KMT21) are dominant for certain diseases but have different severity, penetrance, and age of onset properties.

While it can be expected that population frequency information should be used differently for genes with different inheritance patterns, in the case of FIG. 8A, these two genes are both dominant, but they have other key features that differ (severity, penetrance, age of onset). In conventional variant classification systems, it is difficult to determine how much to adjust the variant pathogenicity probabilities for these two genes to account for these differences.

In contrast, using the population frequency model configured as described, the model output is able to automatically determine the amount by which to adjust the variant pathogenicity probabilities to account for the similar inheritance patterns and different severity, penetrance, and age of onset properties of these two genes, without having been given access to any information about these properties. Even though the model input did not include any information to indicate that these two genes have the same inheritance patterns, or different severity, penetrance, and age of onset, the model has learned, via machine learning-based training and calibration using feature sets as described, that variants in these two genes should be treated differently with respect to the population frequency threshold, and also by how much the probabilities need to be adjusted.

FIG. 8B illustrates another example of population frequency modeling results for a population frequency model configured using a logistic regression model, in accordance with some embodiments of the present disclosure. FIG. 8B shows examples of pathogenicity probabilities that have been estimated and output by the described population frequency model for each variant in two different genes, TSC2 and LAMA2. In FIG. 8B, each dot in the plot represents a different particular variant within a particular gene. The majority of the variants in the gene LAMA2 are plotted in region 822 while the majority of the variants in the gene TSC2 are plotted in region 824. The y axis shows the model output, i.e., the probability of pathogenicity for the variant, and the x axis shows the allele frequency for the variant in a given human population. As the frequency of the variant in the population increases, the probability of pathogenicity decreases.

More specifically, FIG. 8B illustrates an example of the population frequency model configured as described, outputting different variant pathogenicity probabilities for two genes that have similar severity, penetrance, and onset properties but different inheritance patterns. As shown in the table included in FIG. 8B, TSC2 is dominant for a particular disease, while LAMA2 is recessive. The model output supports the intuition that variants in genes that have different inheritance patterns should be held to different population frequency standards. While these differences can be accounted for in conventional variant classification processes by setting different thresholds for recessive and dominant genes, the conventionally used thresholds are still categorical (e.g., recessive, dominant) and often need to be adjusted manually.

In contrast, using the population frequency model configured as described, the model output supports the conventional intuition but without having been given access to any information about inheritance pattern. Even though the model input did not include any information to indicate that these two genes have different inheritance patterns, the model has learned, via machine-learning based training and calibration using feature sets as described, that variants in these two genes should be treated differently with respect to the population frequency threshold, and also by how much the probabilities need to be adjusted.

FIG. 8C illustrates another example of population frequency modeling results for a population frequency model configured using a logistic regression model, in accordance with some embodiments of the present disclosure. FIG. 8C shows examples of pathogenicity probabilities that have been estimated and output by the described population frequency model for each variant in several different genes, EYS, TGM1, CACNA1C, FBN1, and DNAH11. In FIG. 8C, each dot in the plot represents a different particular variant within a particular gene. The majority of the variants in the gene EYS are plotted in region 830, the majority of the variants in the gene TGM1 are plotted in region 832, the majority of the variants in the gene CACNA1C are plotted in region 834, the majority of the variants in the gene FBN1 are plotted in region 836, and the majority of the variants in the gene DNAH11 are plotted in region 838. The y axis shows the model output, i.e., the probability of pathogenicity for the variant, and the x axis shows the allele frequency for the variant in a given human population. As the frequency of the variant in the population increases, the probability of pathogenicity decreases.

More specifically, FIG. 8C illustrates an example of the population frequency model configured as described, outputting different variant pathogenicity probabilities for multiple different genes that have differences that are not intuitive to a variant classification scientist. As shown in the table included in FIG. 8C, these genes have a mix of similarities and differences in the traditional gene-disease attributes. The differences in pathogenicity probability among these genes are not obvious to a human mind, yet the population frequency model configured as described has accounted for these gene-specific differences through the machine learning-based training and calibration processes using feature sets as described. As a result, the pathogenicity curves generated based on the model output show that variants in these genes should be treated differently with respect to the population frequency threshold.

Figure 8D:
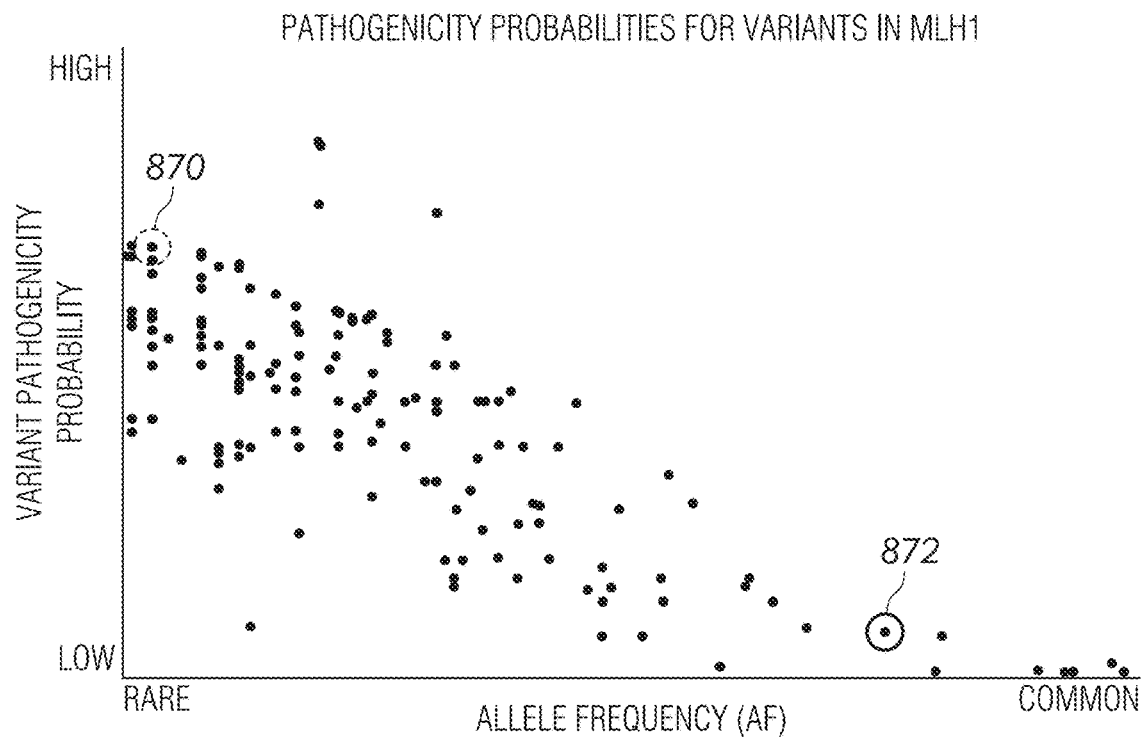
FIG. 8D illustrates another example of population frequency modeling results for a population frequency model configured using a logistic regression model, in accordance with some embodiments of the present disclosure.

FIG. 8D illustrates another example of population frequency modeling results for a population frequency model configured using a logistic regression model, in accordance with some embodiments of the present disclosure. FIG. 8D shows examples of pathogenicity probabilities that have been estimated and output by the described population frequency model for each variant in a given gene, MLH1. In FIG. 8D, each dot in the plot represents a different particular variant. The y axis shows the probability of pathogenicity for the variant, and the x axis shows the allele frequency for the variant in a given human population. As the frequency of the variant in the population increases, the probability of pathogenicity decreases. For the particular variant 870, the model output shows that the variant has a relatively high probability of being pathogenic (i.e., the model output can indicate that the variant is in the pathogenic range, even if the actual probability still may be less than 50%). For the particular variant 872, the model output shows that the probability of being pathogenic is very low. Using a variant classification framework such as Sherloc, in which points are assigned based on evidence of pathogenicity, benign points would not be awarded for variant 870 but would be awarded for variant 872.

Figure 8E:
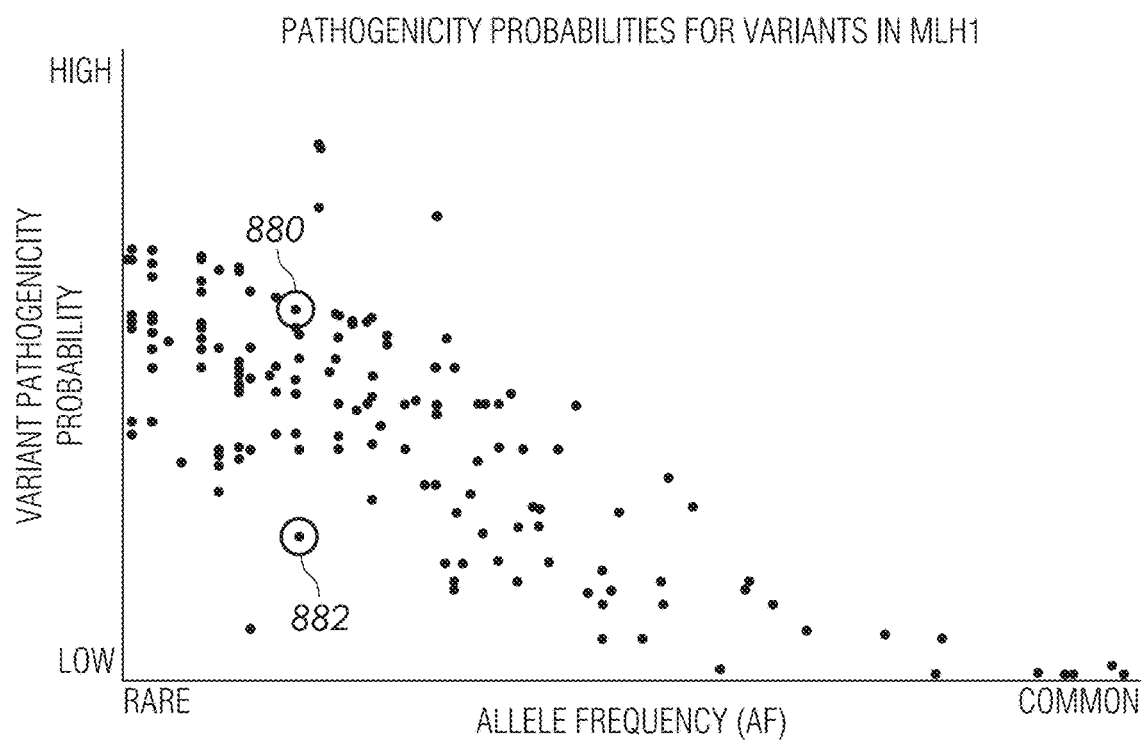
FIG. 8E illustrates another example of population frequency modeling results for a population frequency model configured using a logistic regression model, in accordance with some embodiments of the present disclosure.

FIG. 8E illustrates another example of population frequency modeling results for a population frequency model configured using a logistic regression model, in accordance with some embodiments of the present disclosure. FIG. 8E shows examples of pathogenicity probabilities that have been estimated and output by the described population frequency model for each variant in a given gene, MLH1. In FIG. 8E, each dot in the plot represents a different particular variant. The y axis shows the probability of pathogenicity for the variant, and the x axis shows the allele frequency for the variant in a given human population. As the frequency of the variant in the population increases, the probability of pathogenicity decreases.

In FIG. 8E, the plot is the same as the plot of FIG. 8D but with different variants highlighted for discussion. For the particular variant 880, the model output shows that the variant has a high probability of being pathogenic. For the particular variant 882, the model output shows that the probability of being pathogenic is relatively low even though the allele frequency indicates that the variant 882 is relatively rare.

Additionally, variants 880, 882 of FIG. 8E illustrate the vertical spread for variants within a single gene at a given frequency. This is due to the fact that, in addition to gene-level properties, the population frequency model was provided with, as model input, region-level and position-level properties (e.g., gene-level features, region-level features, and position-level features as described).

FIG. 8E shows that the variant 882 at a given allele frequency is unlikely to be pathogenic, but the variant 880 at the same allele frequency is much more likely to be pathogenic. Conventionally, it can be understood that different parts of the same gene can be more or less tolerant to variation due to, for example, protein domains and functional sequence motifs, and it may be that this low probability variant impacts a region of the gene that is not as important as the high probability variant. However, these differences are hard to address using the conventional variant classification techniques. In contrast, even though the population frequency model was not provided with this domain and motif information, the model configured as described has accounted for these differences through the machine learning-based training and calibration processes using feature sets as described. As a result, the pathogenicity plot generated based on the model output shows that different variants in the same genes should be treated differently with respect to the population frequency threshold.

As such, embodiments of the population frequency model can not only model the expected frequency of a disease for a given gene, but also can determine that different variants in the same gene, with the same frequency, are associated with different probabilities of pathogenicity. Further, embodiments of the model configured as described can discern different allele frequency thresholds for different regions within a gene. This is because the model is trained and calibrated utilizing region level properties in a gene.

FIG. 8F illustrates an example of population frequency modeling results for a population frequency model configured using a logistic regression model, integrated with a variant classification framework in accordance with some embodiments of the present disclosure. In particular, FIG. 8F illustrates how the accuracy of the variant pathogenicity predictions generated and output by embodiments of the population frequency model described (measured as negative and positive predictive values) can be mapped to points in a variant classification system such as Sherloc. While FIG. 8F illustrates an example implementation using the Sherloc framework, the model output can be similarly adapted for incorporation into other variant classification frameworks.

As shown in FIG. 8F, to accommodate the output of the population frequency model, four new lines of evidence were created for the population modeling data for use in Sherloc, where benign and pathogenic points are assigned to each new line of evidence based on the levels of associated accuracy.

For example, a variant with a very highly predictive benign population modeling score, which has a greater than 99% NPV (negative predictive value), is assigned, for example, five benign points and, in the absence of conflicting information from other evidence categories, would be classified as a benign variant using the Sherloc framework.

Conversely, a variant with moderately or highly predictive pathogenic population modeling score, which has a greater than 80% PPV (positive predictive value), is assigned, for example, one point towards pathogenicity and would require, for example, four additional pathogenic points from other independent evidence categories to reach the five point threshold within the Sherloc framework to be classified as a pathogenic.

Population modeling using the modeling approaches described herein can make a significant impact on variant classification. For instance, gnomAD population frequency data can now be applied to four times as many variants as were able to be processed using prior approaches. This expanded use of population frequency data has enabled the reclassification of 15,000 variants from VUS to benign and likely benign variants. For example, 3,146 variants have been reclassified from VUS to benign, and 11,640 variants have been reclassified from VUS to likely benign.

Further, the population frequency model configured as described enables much more efficient use of population frequency data. As a result, many variants of uncertain significance that weren't reclassified based on this data alone are now closer to receiving a definitive classification in the future. The reclassified variants have impacted over 50,000 patients. It is estimated that the described population modeling approach can result in a 2-2.5% reduction in VUS rate for future patients.

Moreover, the described population modeling approach has been applied to variants from diverse populations and to variants across clinical areas. On an aggregate level, this has enabled the identification of subpopulations having the highest frequency for specific variants and the grouping of reclassified variants by primary clinical area.

Figure 9:
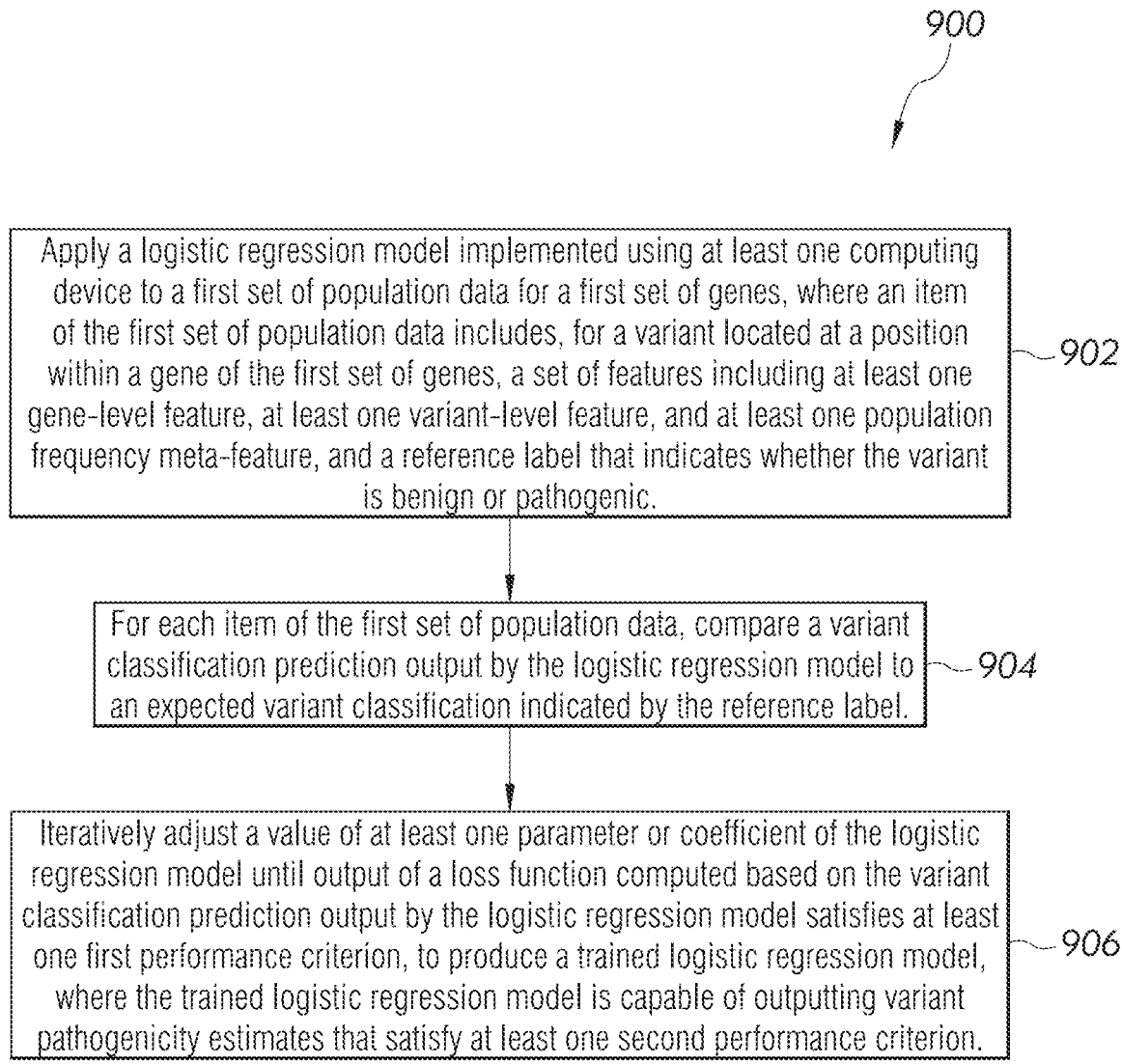
FIG. 9 illustrates a method for population frequency modeling using a population frequency model configured using a logistic regression model, in accordance with some embodiments of the present disclosure.

FIG. 9 illustrates a method 900 for population frequency modeling using a population frequency model configured using a logistic regression model, in accordance with some embodiments of the present disclosure.

The method 900 is performed by processing logic that includes hardware (e.g., processing device, circuitry, dedicated logic, programmable logic, microcode, hardware of a device, integrated circuit, etc.), software (e.g., instructions run or executed on a processing device), or a combination thereof. In some embodiments, the method is performed by components of a computing system, including, in some embodiments, components or flows shown in FIG. 9 that may not be specifically shown in other figures and/or including, in some embodiments, components or flows shown in other figures that may not be specifically shown in FIG. 9. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, at least one process can be omitted in various embodiments. Thus, not all processes are required in every embodiment. Other process flows are possible.

At operation 902, the processing device applies a logistic regression model to a first set of population data for a first set of genes. An item of the first set of population data includes, for a variant located at a position within a gene of the first set of genes, a set of features. The set of features includes at least one gene-level feature, at least one variant-level feature, and at least one population frequency meta-feature. The item of the first set of population data also includes a reference label that indicates whether the variant is benign or pathogenic.

At operation 904, the processing device, for each item of the first set of population data, compares a variant classification prediction output by the logistic regression model to an expected variant classification indicated by the reference label.

At operation 906, the processing device iteratively adjusts a value of at least one parameter or coefficient of the logistic regression model until one or more performance criteria are met, e.g., output of a loss function computed based on the variant classification prediction output by the logistic regression model satisfies at least one first performance criterion (e.g., an error tolerance threshold), to produce a trained logistic regression model (e.g., the model has converged). The trained logistic regression model is capable of outputting variant pathogenicity estimates that satisfy at least one second performance criterion (e.g., one or more validation criteria).

In some implementations, the processing device uses the trained logistic regression model to generate a prediction as to whether a variant is benign or pathogenic. In some implementations, the processing device provides the prediction as to whether the variant is benign or pathogenic to a clinician's computing device for use in formulating, by the clinician, a diagnosis of a patient.

In some implementations, the processing device applies the trained logistic regression model to a second set of population data for a plurality of variants of a second plurality of genes. For each variant of the second plurality of genes, the processing device receives a variant classification prediction output by the trained logistic regression model. In response to the variant classification prediction satisfying at least the second performance criterion, the processing device stores the variant classification prediction in association with the variant for retrieval via at least one query.

In some implementations, the processing device computes a gene-level constraint, includes the gene-level constraint in the at least one gene-level feature, computes an allele frequency, includes the allele frequency in the at least one position-level feature; includes, in the at least one population frequency meta-feature, a mathematical combination of the gene-level constraint and an allele frequency, and applies the logistic regression model to the set of features including the mathematical combination of the gene-level constraint and the allele frequency. The trained logistic regression model is capable of outputting variant pathogenicity estimates that satisfy the at least one second performance criterion based on the set of features including the mathematical combination of the gene-level constraint and the allele frequency.

In some implementations, the processing device computes the allele frequency by calculating a binomial proportion of a confidence value associated with the allele frequency. In some implementations, the processing device computes the mathematical combination of the gene-level constraint and the allele frequency by dividing the allele frequency by the gene-level constraint to produce a quotient and takes an exponent of the quotient.

In some implementations, the processing device computes, for a gene, an exponent of a ratio of synonymous missense variants to nonsynonymous missense variants. The processing device includes the exponent of the ratio of synonymous missense variants to nonsynonymous missense variants in the at least one population frequency meta-feature. The processing device applies the logistic regression model to the set of features including the exponent of the ratio of synonymous missense variants to nonsynonymous missense variants. The trained logistic regression model is capable of outputting variant pathogenicity estimates that satisfy the at least one second performance criterion based on the set of features including the exponent of the ratio of synonymous missense variants to nonsynonymous missense variants.

In some implementations, the processing device selects, as the set of features, not more than thirty features. The processing device applies the logistic regression model to the selected set of not more than thirty features. The trained logistic regression model is capable of outputting variant pathogenicity estimates that satisfy the at least one second performance criterion based on the selected set of not more than thirty features.

In some implementations, the processing device computes a fixation index. The fixation index includes sub-population frequency data. The processing device includes the fixation index in the set of features. The processing device applies the logistic regression model to the set of features including the fixation index. The trained logistic regression model is capable of outputting variant pathogenicity estimates that satisfy the at least one second performance criterion based on the set of features including the fixation index.

In some implementations, the processing device computes, for a variant, a mathematical combination of sub-population frequency data and population frequency data. The processing device includes the mathematical combination of subpopulation frequency data and population frequency data in at least one position-level feature. The processing device applies the logistic regression model to the set of features including the mathematical combination of subpopulation frequency data and population frequency data. The trained logistic regression model is capable of outputting variant pathogenicity estimates that satisfy the at least one second performance criterion based on the set of features including the mathematical combination of subpopulation frequency data and population frequency data.

In some implementations, iteratively adjusting the value of at least one parameter of the logistic regression model includes adjusting a C value of the logistic regression model until the loss satisfies the at least one first performance criterion, to produce the trained logistic regression model. In some implementations, the processing device configures the logistic regression model using L1 regularization. In some implementations, the processing device estimates the first performance criterion using a means square error or area under the receiver operating characteristic curve. In some implementations, the processing device determines the second performance criterion using at least one of decision boundary inspection, feature weight inspection, or a comparison to a benchmark variant classification.

In some implementations, the processing device uses variant classification estimates output by the trained logistic regression model as an input to a variant classification framework. In some implementations, the at least one population frequency meta-feature includes expected frequency distributions of known benign variants and known pathogenic variants within the gene.

Figure 10:
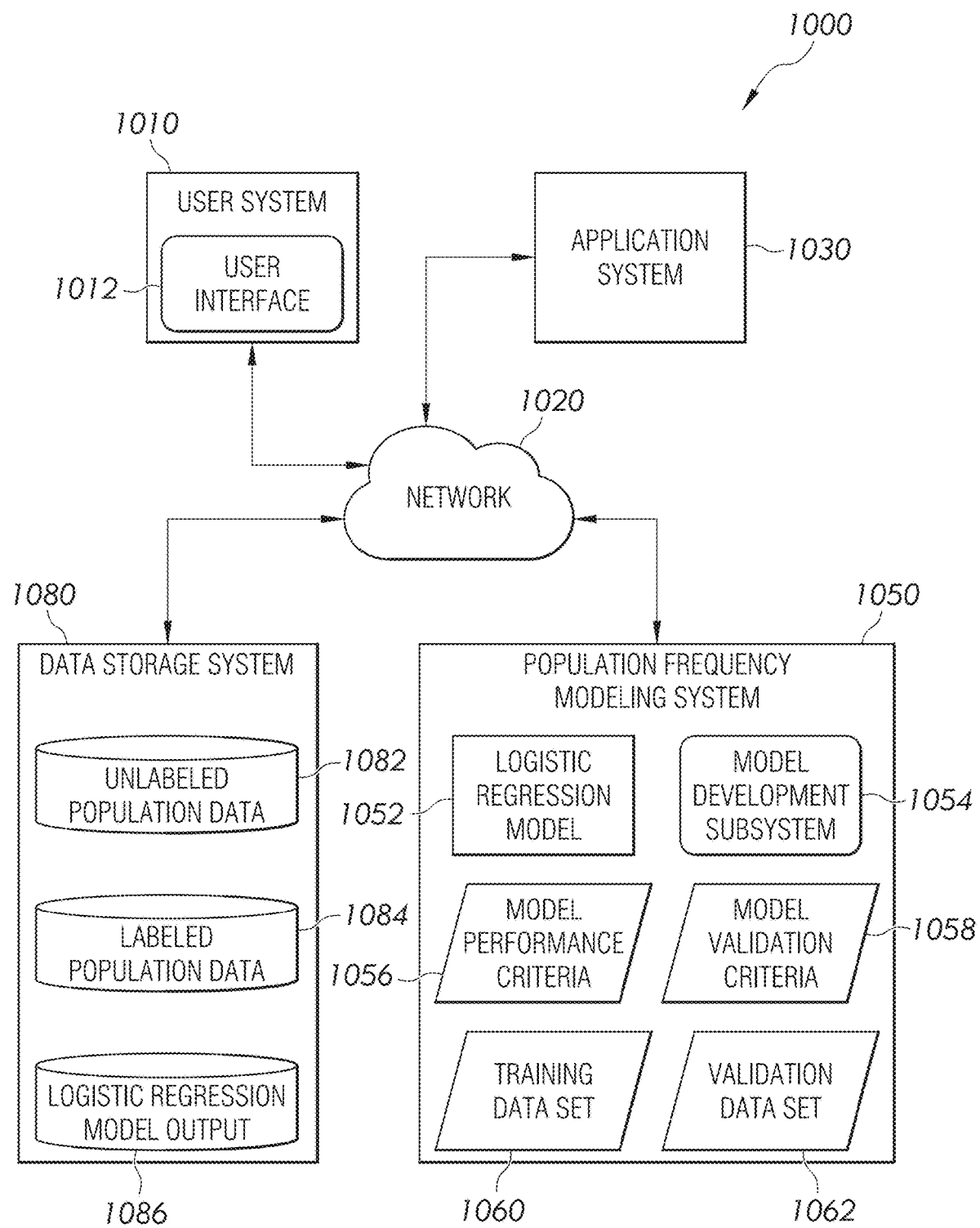
FIG. 10 illustrates an example computing system that includes a population frequency modeling system in accordance with some embodiments of the present disclosure.

FIG. 10 illustrates an example computing system that includes a population frequency modeling system in accordance with some embodiments of the present disclosure. In the embodiment of FIG. 10, computing system 1000 includes one or more user systems 1010, a network 1020, an application system 1030, a population frequency modeling system 1050, and a data storage system 1080.

Population frequency modeling system 1050 includes a logistic regression model 1052, a model development subsystem 1054, model performance criteria 1056, model validation criteria 1058, a training data set 1060, and a validation data set 1062. The components of population frequency modeling system 1050 can correspond to similarly described components shown in other figures and described above. For example, logistic regression model 1052 can correspond to logistic regression model 228 or logistic regression model 306 or trained logistic regression model 604. Model development subsystem 1054 can correspond to a combination of components including gene data selection subsystem 206, feature generation subsystem 212, modeling and calibration subsystem 220, and model validation subsystem 230. Model development subsystem 1054 can be configured to perform process 300 and/or process 400 and/or process 600. Model performance criteria 1056 can correspond to model performance criteria 232. Model validation criteria 1058 can correspond to model validation criteria 236. Training data set 1060 can correspond to training data set 234. Validation data set 1062 can correspond to validation data set 238.

Logistic regression model 1052 includes one or more machine learning models that are trained to determine probabilistic or statistical relationships between inputs and outputs using a machine learning algorithm. For example, given one or more inputs, logistic regression model 1052 outputs labels that can be used to classify the inputs into different categories or scores that can be used to sort or rank the inputs into groups or ranked lists. An example of logistic regression model 1052 is the population frequency model described above.

Model development subsystem 1054 trains the one or more machine learning models of logistic regression model 1052 by, for example, applying a supervised machine learning technique to training data that includes training examples of input data and ground-truth labels. The predictive output of the one or more machine learning models is observed iteratively until a set of model performance criteria are satisfied. For example, differences between predictive output and expected output are quantified using a loss function. The model performance criteria are used to determine when the one or more machine learning models have converged so as to provide output that can be relied upon with some degree of certainty. The requisite level of certainty and the performance criteria are determined based on the requirements or design of a particular implementation of the one or more machine learning models. An example of model development subsystem 1054 includes data preparation, feature engineering, and model selection components, as described above.

Training data set 1060 includes training data used to train the logistic regression model 1052 in some implementations. Training data set 1060 includes, for example, a set of input features and corresponding ground truth labels. Training data set 1060 includes or is derived from a database of historical population data, in some implementations. Examples of training data set 1060 include variant-level data sets, gene-level data sets, and position-level data sets, as described above.

User system 1010 includes at least one computing device, such as a personal computing device, a server, a mobile computing device, or a smart appliance. User system 1010 includes at least one software application, including a user interface 1012, installed on or accessible by a network to a computing device. For example, embodiments of user interface 1012 include a graphical display screen that displays controls and graphical elements for operating and/or manipulating one or more of logistic regression model 1052, model development subsystem 1054, and training data set 1060.

User interface 1012 can be used to input data, initiate user interface events, and view or otherwise perceive output that includes pathogenicity predictions and/or other data produced by population frequency modeling system 1050. Examples of user interface 1012 include web browsers, command line interfaces, and mobile app front ends. User interface 1012 as used herein can include application programming interfaces (APIs). User interface 1012 can include a front end portion of an application system 1030 that is used by a clinician. For example, output of the population frequency modeling system 1050 can be transmitted to and displayed by a user interface 1012 of a computing device used by a clinician. Alternatively or in addition, another version of user interface 1012 can include a front end portion of an application software system 1030 that is used by variant scientists and/or other individuals working in the field of genetic testing. As such, output of the population frequency modeling system 1050 can be transmitted to and displayed by a user interface 1012 of a computing device used by any of these individuals.

Application system 1030 is any type of application software system that provides or enables the generation, display, or manipulation of output produced by population frequency modeling system 1050. Examples of application system 1030 include but are not limited to variant classification systems, DNA (deoxyribonucleic acid) analysis software, genetic testing software, medical testing software, healthcare management software, or any combination of any of the foregoing.

Data storage system 1080 includes data stores and/or data services that store data received, used, manipulated, and produced by application system 1030 and/or population frequency modeling system 1050, such as training data, validation data, machine learning model parameters and coefficients, performance criteria, validation criteria, machine learning model output, etc. In FIG. 10, data storage system 1080 includes one or more data stores that store unlabeled population data 1082, labeled population data 1084, and logistic regression model output 1086. Unlabeled population data can correspond to unlabeled population data 202. Labeled population data 1084 can correspond to labeled population data 204. Logistic regression model output 1086 can correspond to, for example, model output 314, predicted output 414, or model output 606. In some embodiments, data storage system 1080 includes multiple different types of data storage and/or a distributed data service. As used herein, data service may refer to a physical, geographic grouping of machines, a logical grouping of machines, or a single machine. For example, a data service may be a data center, a cluster, a group of clusters, or a machine.

Data storage system 1080 resides on at least one persistent and/or volatile storage device that can reside within the same local network as at least one other device of computing system 1000 and/or in a network that is remote relative to at least one other device of computing system 1000. Thus, although depicted as being included in computing system 1000, portions of data storage system 1080 can be part of computing system 1000 or accessed by computing system 1000 over a network, such as network 1020.

While not specifically shown, it should be understood that any of user system 1010, application system 1030, population frequency modeling system 1050, and data storage system 1080 includes an interface embodied as computer programming code stored in computer memory that when executed causes a computing device to enable bidirectional communication with any other of user system 1010, application system 1030, population frequency modeling system 1050, and data storage system 1080 using a communicative coupling mechanism. Examples of communicative coupling mechanisms include network interfaces, inter-process communication (IPC) interfaces and application program interfaces (APIs).

Each of user system 1010, application system 1030, population frequency modeling system 1050, and data storage system 1080 is implemented using at least one computing device that is communicatively coupled to electronic communications network 1020. Any of user system 1010, application system 1030, population frequency modeling system 1050, and data storage system 1080 can be bidirectionally communicatively coupled by network 1020. User system 1010 as well as other different user systems (not shown) can be bidirectionally communicatively coupled to application system 1030 and/or population frequency modeling system 1050.

A typical user of user system 1010 can be an administrator or end user of application system 1030 and/or population frequency modeling system 1050. User system 1010 is configured to communicate bidirectionally with application system 1030 and/or population frequency modeling system 1050 over network 1020.

The features and functionality of user system 1010, application system 1030, population frequency modeling system 1050, and data storage system 1080 are implemented using computer software, hardware, or software and hardware, and can include combinations of automated functionality, data structures, and digital data, which are represented schematically in the figures. User system 1010, application system 1030, population frequency modeling system 1050, and data storage system 1080 are shown as separate elements in FIG. 10 for ease of discussion but, except as otherwise described, the illustration is not meant to imply that separation of these elements is required. The illustrated systems, services, and data stores (or their functionality) of each of user system 1010, application system 1030, population frequency modeling system 1050, and data storage system 1080 can be divided over any number of physical systems, including a single physical computer system, and can communicate with each other in any appropriate manner.

Network 1020 can be implemented on any medium or mechanism that provides for the exchange of data, signals, and/or instructions between the various components of computing system 1000. Examples of network 1020 include, without limitation, a Local Area Network (LAN), a Wide Area Network (WAN), an Ethernet network or the Internet, or at least one terrestrial, satellite or wireless link, or a combination of any number of different networks and/or communication links.

Figure 11:
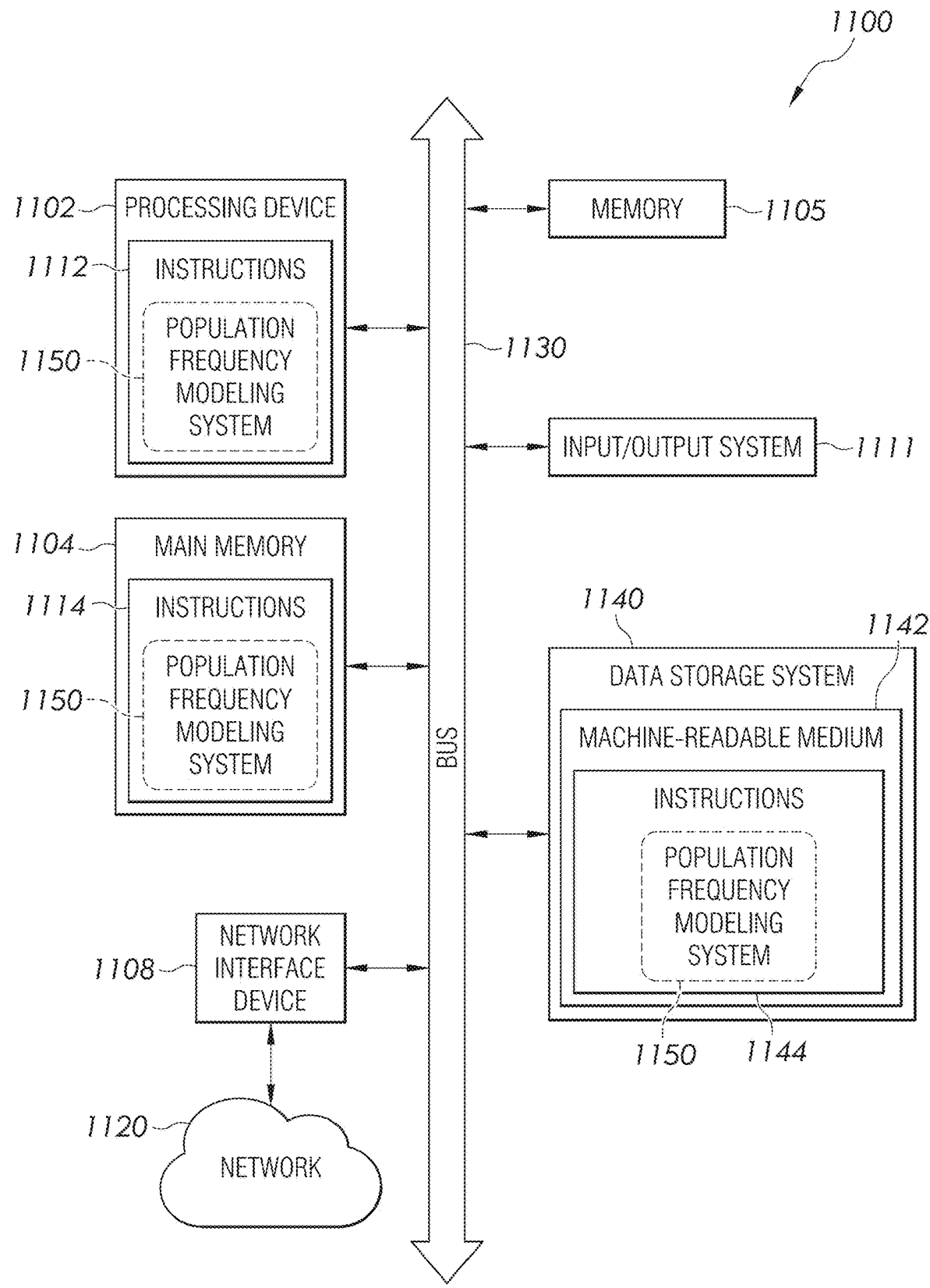
FIG. 11 is a block diagram of an example computer system in which aspects of the present disclosure can operate.

For ease of discussion, in FIG. 11, aspects of the population frequency modeling system 1050 are represented as population frequency modeling system 1150.

FIG. 11 is a block diagram of an example computer system in which aspects of the present disclosure can operate. FIG. 11 illustrates an example machine of a computer system 1100 within which a set of instructions, for causing the machine to perform any of the methodologies discussed herein, can be executed. In some embodiments, the computer system 1100 can correspond to a component of a networked computer system (e.g., the computing system 1000 of FIG. 10) that includes, is coupled to, or utilizes a machine to execute an operating system to perform operations described above corresponding to aspects of the population frequency modeling system 1050 of FIG. 10.

The machine is connected (e.g., networked) to other machines in a local area network (LAN), an intranet, an extranet, and/or the Internet. The machine can operate in the capacity of a server or a client machine in a client-server network environment, as a peer machine in a peer-to-peer (or distributed) network environment, or as a server or a client machine in a cloud computing infrastructure or environment.

The machine is a personal computer (PC), a smart phone, a tablet PC, a set-top box (STB), a Personal Digital Assistant (PDA), a cellular telephone, a web appliance, a server, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any of the methodologies discussed herein.

The example computer system 1100 includes a processing device 1102, a main memory 1104 (e.g., read-only memory (ROM), flash memory, dynamic random access memory (DRAM) such as synchronous DRAM (SDRAM) or Rambus DRAM (RDRAM), etc.), a memory 1105 (e.g., flash memory, static random access memory (SRAM), etc.), an input/output system 1110, and a data storage system 1140, which communicate with each other via a bus 1130.

Processing device 1102 represents at least one general-purpose processing device such as a microprocessor, a central processing unit, or the like. More particularly, the processing device can be a complex instruction set computing (CISC) microprocessor, reduced instruction set computing (RISC) microprocessor, very long instruction word (VLIW) microprocessor, or a processor implementing other instruction sets, or processors implementing a combination of instruction sets. Processing device 1102 can also be at least one special-purpose processing device such as an application specific integrated circuit (ASIC), a field programmable gate array (FPGA), a digital signal processor (DSP), network processor, or the like. The processing device 1102 is configured to execute instructions 1112 for performing the operations and steps discussed herein.

Instructions 1112 include portions of the population frequency modeling system 1150 when those portions of the population frequency modeling system are being executed by processing device 1102. Thus, the population frequency modeling system is shown in dashed lines as part of instructions 1112 to illustrate that, at times, portions of the population frequency modeling system are executed by processing device 1102. For example, when at least some portion of the population frequency modeling system is embodied in instructions to cause processing device 1102 to perform the method(s) described above, some of those instructions can be read into processing device 1102 (e.g., into an internal cache or other memory) from main memory 1104 and/or data storage system 1140. However, it is not required that all of the population frequency modeling system be included in instructions 1112 at the same time and portions of the population frequency modeling system are stored in at least one other component of computer system 1100 at other times, e.g., when at least one portion of the population frequency modeling system are not being executed by processing device 1102.

The computer system 1100 further includes a network interface device 1108 to communicate over the network 1120. Network interface device 1108 provides a two-way data communication coupling to a network. For example, network interface device 1108 can be an integrated-services digital network (ISDN) card, cable modem, satellite modem, or a modem to provide a data communication connection to a corresponding type of telephone line. As another example, network interface device 1108 can be a local area network (LAN) card to provide a data communication connection to a compatible LAN. Wireless links can also be implemented. In any such implementation, network interface device 1108 can send and receive electrical, electromagnetic, or optical signals that carry digital data streams representing various types of information.

The network link can provide data communication through at least one network to other data devices. For example, a network link can provide a connection to the world-wide packet data communication network commonly referred to as the "Internet," for example through a local network to a host computer or to data equipment operated by an Internet Service Provider (ISP). Local networks and the Internet use electrical, electromagnetic, or optical signals that carry digital data to and from computer system 1100.

Computer system 1100 can send messages and receive data, including program code, through the network(s) and network interface device 1108. In the Internet example, a server can transmit a requested code for an application program through the Internet and network interface device 1108. The received code can be executed by processing device 1102 as it is received, and/or stored in data storage system 1140, or other non-volatile storage for later execution.

The input/output system 1110 includes an output device, such as a display, for example a liquid crystal display (LCD) or a touchscreen display, for displaying information to a computer user, or a speaker, a haptic device, or another form of output device. The input/output system 1110 can include an input device, for example, alphanumeric keys and other keys configured for communicating information and command selections to processing device 1102. An input device can, alternatively or in addition, include a cursor control, such as a mouse, a trackball, or cursor direction keys for communicating direction information and command selections to processing device 1102 and for controlling cursor movement on a display. An input device can, alternatively or in addition, include a microphone, a sensor, or an array of sensors, for communicating sensed information to processing device 1102. Sensed information can include voice commands, audio signals, geographic location information, and/or digital imagery, for example.

The data storage system 1140 includes a machine-readable storage medium 1142 (also known as a computer-readable medium) on which is stored at least one set of instructions 1144 or software embodying any of the methodologies or functions described herein. The instructions 1144 can also reside, completely or at least partially, within the main memory 1104 and/or within the processing device 1102 during execution thereof by the computer system 1100, the main memory 1104 and the processing device 1102 also constituting machine-readable storage media.

In one embodiment, the instructions 1144 include instructions to implement functionality corresponding to a population frequency modeling system (e.g., the population frequency modeling system 1050 of FIG. 10).

Dashed lines are used in FIG. 11 to indicate that it is not required that the population frequency modeling system be embodied entirely in instructions 1112, 1114, and 1144 at the same time. In one example, portions of the population frequency modeling system are embodied in instructions 1144, which are read into main memory 1104 as instructions 1114, and portions of instructions 1114 are read into processing device 1102 as instructions 1112 for execution. In another example, some portions of the population frequency modeling system are embodied in instructions 1144 while other portions are embodied in instructions 1114 and still other portions are embodied in instructions 1112.

While the machine-readable storage medium 1142 is shown in an example embodiment to be a single medium, the term "machine-readable storage medium" should be taken to include a single medium or multiple media that store the at least one set of instructions. The term "machine-readable storage medium" shall also be taken to include any medium that is capable of storing or encoding a set of instructions for execution by the machine and that cause the machine to perform any of the methodologies of the present disclosure. The term "machine-readable storage medium" shall accordingly be taken to include, but not be limited to, solid-state memories, optical media, and magnetic media.

Some portions of the preceding detailed descriptions have been presented in terms of algorithms and symbolic representations of operations on data bits within a computer memory. These algorithmic descriptions and representations are the ways used by those skilled in the data processing arts to convey the substance of their work most effectively to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. The present disclosure can refer to the action and processes of a computer system, or similar electronic computing device, which manipulates and transforms data represented as physical (electronic) quantities within the computer system's registers and memories into other data similarly represented as physical quantities within the computer system memories or registers or other such information storage systems.

The present disclosure also relates to an apparatus for performing the operations herein. This apparatus can be specially constructed for the intended purposes, or it can include a general-purpose computer selectively activated or reconfigured by a computer program stored in the computer. For example, a computer system or other data processing system, such as the computing system 1100, can carry out the above-described technologies in response to its processor executing a computer program (e.g., a sequence of instructions) contained in a memory or other non-transitory machine-readable storage medium. Such a computer program can be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general-purpose systems can be used with programs in accordance with the teachings herein, or it can prove convenient to construct a more specialized apparatus to perform the method. The structure for a variety of these systems will appear as set forth in the description below. In addition, the present disclosure is not described with reference to any particular programming language. It will be appreciated that a variety of programming languages can be used to implement the teachings of the disclosure as described herein.

The present disclosure can be provided as a computer program product, or software, which can include a machine-readable medium having stored thereon instructions, which can be used to program a computer system (or other electronic devices) to perform a process according to the present disclosure. A machine-readable medium includes any mechanism for storing information in a form readable by a machine (e.g., a computer). In some embodiments, a machine-readable (e.g., computer-readable) medium includes a machine (e.g., a computer) readable storage medium such as a read only memory ("ROM"), random access memory ("RAM"), magnetic disk storage media, optical storage media, flash memory components, etc.

Illustrative aspects of the technologies disclosed herein are provided below. An embodiment of the technologies may include any of the aspects described herein, or any combination of any of the aspects described herein, or any combination of any portions of the aspects described herein.

In some aspects, the techniques described herein relate to a method for configuring a machine learning model to model population frequency for variant classification, the method including: applying a logistic regression model to a first set of population data for a first set of genes, where an item of the first set of population data includes, for a variant located at a position within a gene of the first set of genes, a set of features including at least one gene-level feature, at least one variant-level feature, and at least one population frequency meta-feature, and a reference label that indicates whether the variant is benign or pathogenic, where the at least one population frequency meta-feature quantifies predictive value of allele frequency in the gene; for each item of the first set of population data, a variant classification prediction output by the logistic regression model an expected variant classification indicated by the reference label; and iteratively adjusting a value of at least one parameter or coefficient of the logistic regression model until the variant classification prediction output by the logistic regression model satisfies at least one first performance criterion, to produce a trained logistic regression model, where the trained logistic regression model is capable of outputting variant pathogenicity estimates that satisfy at least one second performance criterion.

In some aspects, the techniques described herein relate to a method, further including: using the trained logistic regression model to generate a prediction as to whether variant is benign or pathogenic.

In some aspects, the techniques described herein relate to a method, further including: providing the prediction as to whether the variant is benign or pathogenic to a clinician for use in formulating, by the clinician, a diagnosis of a patient.

In some aspects, the techniques described herein relate to a method, further including: applying the trained logistic regression model to a second set of population data for a plurality of variants of a second plurality of genes; and for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

In some aspects, the techniques described herein relate to a method, further including: computing a gene-level constraint; including the gene-level constraint in the at least one gene-level feature; computing an allele frequency; including the allele frequency in the at least one variant-level feature; including, in the at least one population frequency meta-feature, a mathematical combination of the gene-level constraint and an allele frequency; and applying the logistic regression model to the set of features including the mathematical combination of the gene-level constraint and the allele frequency, where the trained logistic regression model is capable of outputting variant pathogenicity estimates that satisfy the at least one second performance criterion based on the set of features including the mathematical combination of the gene-level constraint and the allele frequency.

In some aspects, the techniques described herein relate to a method, further including: computing the allele frequency by calculating a binomial proportion of a confidence value associated with the allele frequency.

In some aspects, the techniques described herein relate to a method, further including: computing the mathematical combination of the gene-level constraint and the allele frequency by dividing the allele frequency by the gene-level constraint to produce a quotient and taking an exponent of the quotient.

In some aspects, the techniques described herein relate to a method, further including: computing, for gene, an exponent of a ratio of synonymous missense variants to nonsynonymous missense variants; including the exponent of the ratio of synonymous missense variants to nonsynonymous missense variants in the at least one population frequency meta-feature; and applying the logistic regression model to the set of features including the exponent of the ratio of synonymous missense variants to nonsynonymous missense variants, where the trained logistic regression model is capable of outputting variant pathogenicity estimates that satisfy the at least one second performance criterion based on the set of features including the exponent of the ratio of synonymous missense variants to nonsynonymous missense variants.

In some aspects, the techniques described herein relate to a method, further including: selecting, as the set of features, not more than thirty features; and applying the logistic regression model to the selected set of not more than thirty features, where the trained logistic regression model is capable of outputting variant pathogenicity estimates that satisfy the at least one second performance criterion based on the selected set of not more than thirty features.

In some aspects, the techniques described herein relate to a method, further including: computing a fixation index, where the fixation index includes sub-population frequency data; including the fixation index in the set of features; and applying the logistic regression model to the set of features including the fixation index, where the trained logistic regression model is capable of outputting variant pathogenicity estimates that satisfy the at least one second performance criterion based on the set of features including the fixation index.

In some aspects, the techniques described herein relate to a method, further including: computing, for a variant, a mathematical combination of subpopulation frequency data and population frequency data; including the mathematical combination of subpopulation frequency data and population frequency data in the at least one variant-level feature; and applying the logistic regression model to the set of features including the mathematical combination of subpopulation frequency data and population frequency data, where the trained logistic regression model is capable of outputting variant pathogenicity estimates that satisfy the at least one second performance criterion based on the set of features including the mathematical combination of subpopulation frequency data and population frequency data.

In some aspects, the techniques described herein relate to a method, where iteratively adjusting the value of at least one parameter of the logistic regression model includes adjusting a C value of the logistic regression model until the satisfies the at least one first performance criterion, to produce the trained logistic regression model.

In some aspects, the techniques described herein relate to a method, further including: configuring the logistic regression model to model population frequency for variant classification using L1 regularization.

In some aspects, the techniques described herein relate to a method, further including: estimating the first performance criterion using a means square error or area under the receiver operating characteristic curve.

In some aspects, the techniques described herein relate to a method, further including: determining the second performance criterion using at least one of decision boundary inspection, feature weight inspection, or a comparison to a benchmark variant classification.

In some aspects, the techniques described herein relate to a method, further including: using variant classification estimates output by the trained logistic regression model as an input to a classification framework.

In some aspects, the techniques described herein relate to a method, where the at least one population frequency meta-feature includes expected frequency distributions of known benign variants and known pathogenic variants within the gene.

In some aspects, the techniques described herein relate to a system, including: at least one processor; and at least one memory coupled to the at least one processor, where the at least one memory includes at least one instruction that when executed by the at least one processor causes the at least one processor to perform at least one operation including: applying a logistic regression model to a first set of population data for a first set of genes, where an item of the first set of population data includes, for a variant located at a position within a gene of the first set of genes, a set of features including at least one gene-level feature, at least one variant-level feature, and at least one population frequency meta-feature, and a reference label that indicates whether the variant is benign or pathogenic, where the at least one population frequency meta-feature quantifies predictive value of allele frequency in the gene; for each item of the first set of population data, a variant classification prediction output by the logistic regression model an expected variant classification indicated by the reference label; and adjusting a value of at least one parameter or coefficient of the logistic regression model until at least one first performance criterion is satisfied to produce a trained logistic regression model, where the trained logistic regression model is capable of outputting variant pathogenicity estimates that satisfy at least one second performance criterion.

In some aspects, the techniques described herein relate to a system, where the at least one memory further includes at least one instruction that when executed by the at least one processor causes the at least one processor to perform at least one operation including: using the trained logistic regression model to generate a prediction as to whether variant is benign or pathogenic.

In some aspects, the techniques described herein relate to a system, where the at least one memory further includes at least one instruction that when executed by the at least one processor causes the at least one processor to perform at least one operation including: providing the prediction as to whether the variant is benign or pathogenic to a clinician for use in formulating, by the clinician, a diagnosis of a patient.

In some aspects, the techniques described herein relate to a system, where the at least one memory further includes at least one instruction that when executed by the at least one processor causes the at least one processor to perform at least one operation including: applying the trained logistic regression model to a second set of population data for a plurality of variants of a second plurality of genes; and for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

In some aspects, the techniques described herein relate to a system, where the at least one memory further includes at least one instruction that when executed by the at least one processor causes the at least one processor to perform at least one operation including: computing a gene-level constraint; including the gene-level constraint in the at least one gene-level feature; computing an allele frequency; including the allele frequency in the at least one variant-level feature; including, in the at least one population frequency meta-feature, a mathematical combination of the gene-level constraint and an allele frequency; and applying the logistic regression model to the set of features including the mathematical combination of the gene-level constraint and the allele frequency, where the trained logistic regression model is capable of outputting variant pathogenicity estimates that satisfy the at least one second performance criterion based on the set of features including the mathematical combination of the gene-level constraint and the allele frequency.

In some aspects, the techniques described herein relate to a system, where the at least one memory further includes at least one instruction that when executed by the at least one processor causes the at least one processor to perform at least one operation including: computing the allele frequency by calculating a binomial proportion of a confidence value associated with the allele frequency.

In some aspects, the techniques described herein relate to a system, where the at least one memory further includes at least one instruction that when executed by the at least one processor causes the at least one processor to perform at least one operation including: computing the mathematical combination of the gene-level constraint and the allele frequency by dividing the allele frequency by the gene-level constraint to produce a quotient and taking an exponent of the quotient.

In some aspects, the techniques described herein relate to a system, where the at least one memory further includes at least one instruction that when executed by the at least one processor causes the at least one processor to perform at least one operation including: computing, for gene, an exponent of a ratio of synonymous missense variants to nonsynonymous missense variants; including the exponent of the ratio of synonymous missense variants to nonsynonymous missense variants in the at least one population frequency meta-feature; and applying the logistic regression model to the set of features including the exponent of the ratio of synonymous missense variants to nonsynonymous missense variants, where the trained logistic regression model is capable of outputting variant pathogenicity estimates that satisfy the at least one second performance criterion based on the set of features including the exponent of the ratio of synonymous missense variants to nonsynonymous missense variants.

In some aspects, the techniques described herein relate to a system, where the at least one memory further includes at least one instruction that when executed by the at least one processor causes the at least one processor to perform at least one operation including: selecting, as the set of features, not more than thirty features; and applying the logistic regression model to the selected set of not more than thirty features, where the trained logistic regression model is capable of outputting variant pathogenicity estimates that satisfy the at least one second performance criterion based on the selected set of not more than thirty features.

In some aspects, the techniques described herein relate to a system, where the at least one memory further includes at least one instruction that when executed by the at least one processor causes the at least one processor to perform at least one operation including: computing a fixation index, where the fixation index includes sub-population frequency data; including the fixation index in the set of features; and applying the logistic regression model to the set of features including the fixation index, where the trained logistic regression model is capable of outputting variant pathogenicity estimates that satisfy the at least one second performance criterion based on the set of features including the fixation index.

In some aspects, the techniques described herein relate to a system, where the at least one memory further includes at least one instruction that when executed by the at least one processor causes the at least one processor to perform at least one operation including: computing, for a variant, a mathematical combination of subpopulation frequency data and population frequency data; including the mathematical combination of subpopulation frequency data and population frequency data in the at least one variant-level feature; and applying the logistic regression model to the set of features including the mathematical combination of subpopulation frequency data and population frequency data, where the trained logistic regression model is capable of outputting variant pathogenicity estimates that satisfy the at least one second performance criterion based on the set of features including the mathematical combination of subpopulation frequency data and population frequency data.

In some aspects, the techniques described herein relate to a system, where iteratively adjusting the value of at least one parameter of the logistic regression model includes adjusting a C value of the logistic regression model until the satisfies the at least one first performance criterion, to produce the trained logistic regression model.

In some aspects, the techniques described herein relate to a system, where the at least one memory further includes at least one instruction that when executed by the at least one processor causes the at least one processor to perform at least one operation including: configuring the logistic regression model to model population frequency for variant classification using L1 regularization.

In some aspects, the techniques described herein relate to a system, where the at least one memory further includes at least one instruction that when executed by the at least one processor causes the at least one processor to perform at least one operation including: estimating the first performance criterion using a means square error or area under the receiver operating characteristic curve.

In some aspects, the techniques described herein relate to a system, where the at least one memory further includes at least one instruction that when executed by the at least one processor causes the at least one processor to perform at least one operation including: determining the second performance criterion using at least one of decision boundary inspection, feature weight inspection, or a comparison to a benchmark variant classification.

In some aspects, the techniques described herein relate to a system, where the at least one memory further includes at least one instruction that when executed by the at least one processor causes the at least one processor to perform at least one operation including: using variant classification estimates output by the trained logistic regression model as an input to a classification framework.

In some aspects, the techniques described herein relate to a system, where the at least one population frequency meta-feature includes expected frequency distributions of known benign variants and known pathogenic variants within the gene.

In some aspects, the techniques described herein relate to at least one non-transitory machine-readable medium including at least one instruction that when executed by at least one processor causes the at least one processor to perform operations including: applying a logistic regression model to a first set of population data for a first set of genes, where an item of the first set of population data includes, for a variant located at a position within a gene of the first set of genes, a set of features including at least one population frequency meta-feature and a reference label that indicates whether the variant is benign or pathogenic, where the at least one population frequency meta-feature quantifies predictive value of allele frequency in the gene; for each item of the first set of population data, a variant classification prediction output by the logistic regression model an expected variant classification indicated by the reference label; and adjusting a value of at least one parameter or coefficient of the logistic regression model until at least one first performance criterion is satisfied to produce a trained logistic regression model, where the trained logistic regression model is capable of outputting variant pathogenicity estimates that satisfy at least one second performance criterion.

In some aspects, the techniques described herein relate to an at least one non-transitory machine-readable medium, further including at least one instruction that when executed by the at least one processor causes the at least one processor to perform at least one operation including: using the trained logistic regression model to generate a prediction as to whether variant is benign or pathogenic.

In some aspects, the techniques described herein relate to an at least one non-transitory machine-readable medium, further including at least one instruction that when executed by the at least one processor causes the at least one processor to perform at least one operation including: providing the prediction as to whether the variant is benign or pathogenic to a clinician for use in formulating, by the clinician, a diagnosis of a patient.

In some aspects, the techniques described herein relate to an at least one non-transitory machine-readable medium, further including at least one instruction that when executed by the at least one processor causes the at least one processor to perform at least one operation including: applying the trained logistic regression model to a second set of population data for a plurality of variants of a second plurality of genes; and for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

In some aspects, the techniques described herein relate to an at least one non-transitory machine-readable medium, further including at least one instruction that when executed by the at least one processor causes the at least one processor to perform at least one operation including: computing a gene-level constraint; computing an allele frequency; including, in the at least one population frequency meta-feature, a mathematical combination of the gene-level constraint and the allele frequency; and applying the logistic regression model to the set of features including the mathematical combination of the gene-level constraint and the allele frequency, where the trained logistic regression model is capable of outputting variant pathogenicity estimates that satisfy the at least one second performance criterion based on the set of features including the mathematical combination of the gene-level constraint and the allele frequency.

In some aspects, the techniques described herein relate to an at least one non-transitory machine-readable medium, further including at least one instruction that when executed by the at least one processor causes the at least one processor to perform at least one operation including: computing the allele frequency by calculating a binomial proportion of a confidence value associated with the allele frequency.

In some aspects, the techniques described herein relate to an at least one non-transitory machine-readable medium, further including at least one instruction that when executed by the at least one processor causes the at least one processor to perform at least one operation including: computing the mathematical combination of the gene-level constraint and the allele frequency by dividing the allele frequency by the gene-level constraint to produce a quotient and taking an exponent of the quotient.

In some aspects, the techniques described herein relate to an at least one non-transitory machine-readable medium, further including at least one instruction that when executed by the at least one processor causes the at least one processor to perform at least one operation including: computing, for gene, an exponent of a ratio of synonymous missense variants to nonsynonymous missense variants; including the exponent of the ratio of synonymous missense variants to nonsynonymous missense variants in the at least one population frequency meta-feature; and applying the logistic regression model to the set of features including the exponent of the ratio of synonymous missense variants to nonsynonymous missense variants, where the trained logistic regression model is capable of outputting variant pathogenicity estimates that satisfy the at least one second performance criterion based on the set of features including the exponent of the ratio of synonymous missense variants to nonsynonymous missense variants.

In some aspects, the techniques described herein relate to an at least one non-transitory machine-readable medium, further including at least one instruction that when executed by the at least one processor causes the at least one processor to perform at least one operation including: selecting, as the set of features, not more than thirty features; and applying the logistic regression model to the selected set of not more than thirty features, where the trained logistic regression model is capable of outputting variant pathogenicity estimates that satisfy the at least one second performance criterion based on the selected set of not more than thirty features.

In some aspects, the techniques described herein relate to an at least one non-transitory machine-readable medium further including at least one instruction that when executed by the at least one processor causes the at least one processor to perform at least one operation including: computing a fixation index, where the fixation index includes sub-population frequency data; including the fixation index in the set of features; and applying the logistic regression model to the set of features including the fixation index, where the trained logistic regression model is capable of outputting variant pathogenicity estimates that satisfy the at least one second performance criterion based on the set of features including the fixation index.

In some aspects, the techniques described herein relate to an at least one non-transitory machine-readable medium, further including at least one instruction that when executed by the at least one processor causes the at least one processor to perform at least one operation including: computing, for a variant, a mathematical combination of subpopulation frequency data and population frequency data; and applying the logistic regression model to the set of features including the mathematical combination of subpopulation frequency data and population frequency data, where the trained logistic regression model is capable of outputting variant pathogenicity estimates that satisfy the at least one second performance criterion based on the set of features including the mathematical combination of subpopulation frequency data and population frequency data.

In some aspects, the techniques described herein relate to an at least one non-transitory machine-readable medium, where adjusting the value of at least one parameter of the logistic regression model includes adjusting a C value of the logistic regression model until satisfies the at least one first performance criterion, to produce the trained logistic regression model.

In some aspects, the techniques described herein relate to an at least one non-transitory machine-readable medium, further including at least one instruction that when executed by the at least one processor causes the at least one processor to perform at least one operation including: configuring the logistic regression model to model population frequency for variant classification using L1 regularization.

In some aspects, the techniques described herein relate to an at least one non-transitory machine-readable medium, further including at least one instruction that when executed by the at least one processor causes the at least one processor to perform at least one operation including: estimating the at least one first performance criterion using a means square error or area under the receiver operating characteristic curve.

In some aspects, the techniques described herein relate to an at least one non-transitory machine-readable medium, further including at least one instruction that when executed by the at least one processor causes the at least one processor to perform at least one operation including: determining the second performance criterion using at least one of decision boundary inspection, feature weight inspection, or a comparison to a benchmark variant classification.

In some aspects, the techniques described herein relate to an at least one non-transitory machine-readable medium, further including at least one instruction that when executed by the at least one processor causes the at least one processor to perform at least one operation including: using variant classification estimates output by the trained logistic regression model as an input to a classification framework.

In some aspects, the techniques described herein relate to an at least one non-transitory machine-readable medium, where the at least one population frequency meta-feature includes expected frequency distributions of known benign variants and known pathogenic variants within the gene.

In some aspects the techniques described herein related to any one or more aspects, steps, components, elements, processes, or limitations that are at least one of described in the enclosed description or shown in the accompanying drawings.

In the foregoing specification, embodiments of the disclosure have been described with reference to specific example embodiments thereof. It will be evident that various modifications can be made thereto without departing from the broader spirit and scope of embodiments of the disclosure as set forth in the following claims. The specification and drawings are, accordingly, to be regarded in an illustrative sense rather than a restrictive sense.

What is claimed is:

1. A method for configuring a machine learning model to model population frequency for variant classification, the method comprising:
   applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene, wherein the applying comprises computing a gene-level constraint; including the gene-level constraint in the at least one gene-level feature; computing an allele frequency; including the allele frequency in the at least one variant-level feature; including, in the at least one population frequency meta-feature, a mathematical combination of the gene-level constraint and the allele frequency;
   and applying the logistic regression model to the set of features including the mathematical combination of the gene-level constraint and the allele frequency; wherein the trained logistic regression model is capable of outputting variant pathogenicity estimates that satisfy the at least one second performance criterion based on the set of features including the mathematical combination of the gene-level constraint and the allele frequency;
   for each item of the first set of population data, evaluating a variant classification prediction output by the logistic regression model based on an expected variant classification indicated by the reference label; and
   iteratively adjusting a value of at least one parameter or coefficient of the logistic regression model until output of a loss function computed based on the variant classification prediction output by the logistic regression model satisfies at least one first performance criterion, to produce a trained logistic regression model, wherein the trained logistic regression model is capable of outputting variant pathogenicity estimates that satisfy at least one second performance criterion.

2. The method of claim 1, further comprising:
   using the trained logistic regression model to generate a prediction as to whether the variant is benign or pathogenic.

3. The method of claim 2, further comprising:
   providing the prediction as to whether the variant is benign or pathogenic to a clinician for use in formulating, by the clinician, a diagnosis of a patient.

4. The method of claim 1, further comprising:
   applying the trained logistic regression model to a second set of population data for a plurality of variants of a second plurality of genes; and
   for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

5. The method of claim 1, further comprising:
computing the allele frequency by calculating a binomial proportion of a confidence value associated with the allele frequency.

6. The method of claim 1, further comprising:
computing the mathematical combination of the gene-level constraint and the allele frequency by dividing the allele frequency by the gene-level constraint to produce a quotient and taking an exponent of the quotient.

7. A method for configuring a machine learning model to model population frequency for variant classification, the method comprising:
applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene;
for each item of the first set of population data, evaluating a variant classification prediction output by the logistic regression model based on an expected variant classification indicated by the reference label;
iteratively adjusting a value of at least one parameter or coefficient of the logistic regression model until output of a loss function computed based on the variant classification prediction output by the logistic regression model satisfies at least one first performance criterion, to produce a trained logistic regression model, wherein the trained logistic regression model is capable of outputting variant pathogenicity estimates that satisfy at least one second performance criterion;
computing, for the gene, an exponent of a ratio of synonymous missense variants to nonsynonymous missense variants;
including the exponent of the ratio of synonymous missense variants to nonsynonymous missense variants in the at least one population frequency meta-feature; and
applying the logistic regression model to the set of features including the exponent of the ratio of synonymous missense variants to nonsynonymous missense variants, wherein the trained logistic regression model is capable of outputting variant pathogenicity estimates that satisfy the at least one second performance criterion based on the set of features including the exponent of the ratio of synonymous missense variants to nonsynonymous missense variants.

8. The method of claim 1, further comprising:
selecting, as the set of features, not more than thirty features; and
applying the logistic regression model to the selected set of not more than thirty features, wherein the trained logistic regression model is capable of outputting variant pathogenicity estimates that satisfy the at least one second performance criterion based on the selected set of not more than thirty features.

9. The method of claim 1, further comprising:
computing a fixation index, wherein the fixation index comprises sub-population frequency data;
including the fixation index in the set of features; and
applying the logistic regression model to the set of features including the fixation index, wherein the trained logistic regression model is capable of outputting variant pathogenicity estimates that satisfy the at least one second performance criterion based on the set of features including the fixation index.

10. A method for configuring a machine learning model to model population frequency for variant classification, the method comprising:
applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene;
for each item of the first set of population data, evaluating a variant classification prediction output by the logistic regression model based on an expected variant classification indicated by the reference label;
iteratively adjusting a value of at least one parameter or coefficient of the logistic regression model until output of a loss function computed based on the variant classification prediction output by the logistic regression model satisfies at least one first performance criterion, to produce a trained logistic regression model, wherein the trained logistic regression model is capable of outputting variant pathogenicity estimates that satisfy at least one second performance criterion;
computing, for a variant, a mathematical combination of subpopulation frequency data and population frequency data;
including the mathematical combination of subpopulation frequency data and population frequency data in the at least one variant-level feature; and
applying the logistic regression model to the set of features including the mathematical combination of subpopulation frequency data and population frequency data, wherein the trained logistic regression model is capable of outputting variant pathogenicity estimates that satisfy the at least one second performance criterion based on the set of features including the mathematical combination of subpopulation frequency data and population frequency data.

11. The method of claim 1, wherein iteratively adjusting the value of at least one parameter of the logistic regression model comprises adjusting a C value of the logistic regression model until the output of the loss function satisfies the at least one first performance criterion, to produce the trained logistic regression model.

12. The method of claim 1, further comprising:
configuring the logistic regression model to model population frequency for variant classification using L1 regularization.

13. The method of claim 1, further comprising:
estimating the first performance criterion using a means square error or area under the receiver operating characteristic curve.

14. The method of claim 1, further comprising:
determining the second performance criterion using at least one of decision boundary inspection, feature weight inspection, or a comparison to a benchmark variant classification.

15. The method of claim 1, further comprising:
using variant classification estimates output by the trained logistic regression model as an input to a variant classification framework.

16. The method of claim 1, wherein the at least one population frequency meta-feature comprises expected frequency distributions of known benign variants and known pathogenic variants within the gene.

17. A system, comprising:
at least one processor; and
at least one memory coupled to the at least one processor, wherein the at least one memory comprises at least one instruction that when executed by the at least one processor causes the at least one processor to perform at least one operation comprising:
applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene, wherein the applying comprises computing a gene-level constraint; including the gene-level constraint in the at least one gene-level feature; computing an allele frequency; including the allele frequency in the at least one variant-level feature; including, in the at least one population frequency meta-feature, a mathematical combination of the gene-level constraint and the allele frequency; and applying the logistic regression model to the set of features including the mathematical combination of the gene-level constraint and the allele frequency; wherein the trained logistic regression model is capable of outputting variant pathogenicity estimates that satisfy the at least one second performance criterion based on the set of features including the mathematical combination of the gene-level constraint and the allele frequency;
for each item of the first set of population data, evaluating a variant classification prediction indicated by the reference label; and
adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion.

18. The system of claim 17, wherein the at least one memory further comprises at least one instruction that when executed by the at least one processor causes the at least one processor to perform at least one operation comprising:
using the trained logistic regression model to generate a prediction as to whether the variant is benign or pathogenic.

19. The system of claim 18, wherein the at least one memory further comprises at least one instruction that when executed by the at least one processor causes the at least one processor to perform at least one operation comprising:
providing the prediction as to whether the variant is benign or pathogenic to a clinician for use in formulating, by the clinician, a diagnosis of a patient.

20. The system of claim 17, wherein the at least one memory further comprises at least one instruction that when executed by the at least one processor causes the at least one processor to perform at least one operation comprising:
applying the trained logistic regression model to a second set of population data for a plurality of variants of a second plurality of genes; and
for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

21. The system of claim 17, wherein the at least one memory further comprises at least one instruction that when executed by the at least one processor causes the at least one processor to perform at least one operation comprising:
computing the allele frequency by calculating a binomial proportion of a confidence value associated with the allele frequency.

22. The system of claim 17, wherein the at least one memory further comprises at least one instruction that when executed by the at least one processor causes the at least one processor to perform at least one operation comprising:
computing the mathematical combination of the gene-level constraint and the allele frequency by dividing the allele frequency by the gene-level constraint to produce a quotient and taking an exponent of the quotient.

23. A system, comprising:
at least one processor; and
at least one memory coupled to the at least one processor, wherein the at least one memory comprises at least one instruction that when executed by the at least one processor causes the at least one processor to perform at least one operation comprising:
applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene;
for each item of the first set of population data, evaluating a variant classification prediction indicated by the reference label;
adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion;
computing, for the gene, an exponent of a ratio of synonymous missense variants to nonsynonymous missense variants;
including the exponent of the ratio of synonymous missense variants to nonsynonymous missense variants in the at least one population frequency meta-feature; and
applying the logistic regression model to the set of features including the exponent of the ratio of synonymous missense variants to nonsynonymous missense variants, wherein the trained logistic regression model is capable of outputting variant pathogenicity estimates that satisfy the at least one second performance criterion based on the set of features including the exponent of the ratio of synonymous missense variants to non-synonymous missense variants.

24. The system of claim 17, wherein the at least one memory further comprises at least one instruction that when executed by the at least one processor causes the at least one processor to perform at least one operation comprising:
selecting, as the set of features, not more than thirty features; and
applying the logistic regression model to the selected set of not more than thirty features, wherein the trained logistic regression model is capable of outputting variant pathogenicity estimates that satisfy the at least one second performance criterion based on the selected set of not more than thirty features.

25. The system of claim 17, wherein the at least one memory further comprises at least one instruction that when executed by the at least one processor causes the at least one processor to perform at least one operation comprising:
computing a fixation index, wherein the fixation index comprises sub-population frequency data;
including the fixation index in the set of features; and
applying the logistic regression model to the set of features including the fixation index, wherein the trained logistic regression model is capable of outputting variant pathogenicity estimates that satisfy the at least one second performance criterion based on the set of features including the fixation index.

26. A system, comprising:
at least one processor; and
at least one memory coupled to the at least one processor, wherein the at least one memory comprises at least one instruction that when executed by the at least one processor causes the at least one processor to perform at least one operation comprising:
applying a logistic regression model to a first set of population data for a first set of genes, wherein an item of the first set of population data comprises, for a variant located at a position within a gene of the first set of genes, a set of features comprising at least one gene-level feature, at least one variant-level feature, and at least one population frequency meta-feature, and a reference label that indicates whether the variant is benign or pathogenic, wherein the at least one population frequency meta-feature quantifies predictive value of allele frequency in the gene;
for each item of the first set of population data, evaluating a variant classification prediction output by the logistic regression model based on an expected variant classification indicated by the reference label;
adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion;
computing, for a variant, a mathematical combination of subpopulation frequency data and population frequency data;
including the mathematical combination of subpopulation frequency data and population frequency data in the at least one variant-level feature; and
applying the logistic regression model to the set of features including the mathematical combination of subpopulation frequency data and population frequency data, wherein the trained logistic regression model is capable of outputting variant pathogenicity estimates that satisfy the at least one second performance criterion based on the set of features including the mathematical combination of subpopulation frequency data and population frequency data.

27. The system of claim 17, wherein iteratively adjusting the value of at least one parameter of the logistic regression model comprises adjusting a C value of the logistic regression model until the output of the loss function satisfies the at least one first performance criterion, to produce the trained logistic regression model.

28. The system of claim 17, wherein the at least one memory further comprises at least one instruction that when executed by the at least one processor causes the at least one processor to perform at least one operation comprising:
configuring the logistic regression model to model population frequency for variant classification using L1 regularization.

29. The system of claim 17, wherein the at least one memory further comprises at least one instruction that when executed by the at least one processor causes the at least one processor to perform at least one operation comprising:
estimating the first performance criterion using a means square error or area under the receiver operating characteristic curve.

30. The system of claim 17, wherein the at least one memory further comprises at least one instruction that when executed by the at least one processor causes the at least one processor to perform at least one operation comprising:
determining the second performance criterion using at least one of decision boundary inspection, feature weight inspection, or a comparison to a benchmark variant classification.

31. The system of claim 17, wherein the at least one memory further comprises at least one instruction that when executed by the at least one processor causes the at least one processor to perform at least one operation comprising:
using variant classification estimates output by the trained logistic regression model as an input to a variant classification framework.

32. The system of claim 17, wherein the at least one population frequency meta-feature comprises expected frequency distributions of known benign variants and known pathogenic variants within the gene.

33. At least one non-transitory machine-readable medium comprising at least one instruction that when executed by at least one processor causes the at least one processor to perform operations comprising:
applying a logistic regression model to a first set of population data for a first set of genes, wherein an item of the first set of population data comprises, for a variant located at a position within a gene of the first set of genes, a set of features comprising at least one population frequency meta-feature and a reference label that indicates whether the variant is benign or pathogenic, wherein the at least one population frequency meta-feature quantifies predictive value of allele frequency in the gene, wherein the applying comprises computing a gene-level constraint; including the gene-level constraint in the at least one gene-level feature; computing an allele frequency; including the allele frequency in the at least one variant-level feature; including, in the at least one population frequency meta-feature, a mathematical combination of the gene-level constraint and the allele frequency; and applying the logistic regression model to the set of features including the mathematical combination of the gene-level constraint and the allele frequency; wherein the trained logistic regression model is capable of outputting variant pathogenicity estimates that satisfy the at least one second performance criterion based on the set of features including the mathematical combination of the gene-level constraint and the allele frequency;

for each item of the first set of population data, evaluating a variant classification prediction indicated by the reference label; and adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion.

34. The at least one non-transitory machine-readable medium of claim 33, further comprising at least one instruction that when executed by the at least one processor causes the at least one processor to perform at least one operation comprising:

using the trained logistic regression model to generate a prediction as to whether the variant is benign or pathogenic.

35. The at least one non-transitory machine-readable medium of claim 34, further comprising at least one instruction that when executed by the at least one processor causes the at least one processor to perform at least one operation comprising:

providing the prediction as to whether the variant is benign or pathogenic to a clinician for use in formulating, by the clinician, a diagnosis of a patient.

36. The at least one non-transitory machine-readable medium of claim 33, further comprising at least one instruction that when executed by the at least one processor causes the at least one processor to perform at least one operation comprising:

applying the trained logistic regression model to a second set of population data for a plurality of variants of a second plurality of genes; and for each variant of the second plurality of genes, receiving a variant classification prediction output by the trained logistic regression model and, in response to the variant classification prediction satisfying at least the second performance criterion, storing the variant classification prediction in association with the variant for retrieval via at least one query.

37. The at least one non-transitory machine-readable medium of claim 33, further comprising at least one instruction that when executed by the at least one processor causes the at least one processor to perform at least one operation comprising:

computing the allele frequency by calculating a binomial proportion of a confidence value associated with the allele frequency.

38. The at least one non-transitory machine-readable medium of claim 33, further comprising at least one instruction that when executed by the at least one processor causes the at least one processor to perform at least one operation comprising:

computing the mathematical combination of the gene-level constraint and the allele frequency by dividing the allele frequency by the gene-level constraint to produce a quotient and taking an exponent of the quotient.

39. At least one non-transitory machine-readable medium comprising at least one instruction that when executed by at least one processor causes the at least one processor to perform operations comprising:

applying a logistic regression model to a first set of population data for a first set of genes, wherein an item of the first set of population data comprises, for a variant located at a position within a gene of the first set of genes, a set of features comprising at least one population frequency meta-feature and a reference label that indicates whether the variant is benign or pathogenic, wherein the at least one population frequency meta-feature quantifies predictive value of allele frequency in the gene;

for each item of the first set of population data, evaluating a variant classification prediction indicated by the reference label;

adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion;

computing, for the gene, an exponent of a ratio of synonymous missense variants to nonsynonymous missense variants;

including the exponent of the ratio of synonymous missense variants to nonsynonymous missense variants in the at least one population frequency meta-feature; and applying the logistic regression model to the set of features including the exponent of the ratio of synonymous missense variants to nonsynonymous missense variants, wherein the trained logistic regression model is capable of outputting variant pathogenicity estimates that satisfy the at least one second performance criterion based on the set of features including the exponent of the ratio of synonymous missense variants to nonsynonymous missense variants.

40. The at least one non-transitory machine-readable medium of claim 33, further comprising at least one instruction that when executed by the at least one processor causes the at least one processor to perform at least one operation comprising:

selecting, as the set of features, not more than thirty features; and applying the logistic regression model to the selected set of not more than thirty features, wherein the trained logistic regression model is capable of outputting variant pathogenicity estimates that satisfy the at least one second performance criterion based on the selected set of not more than thirty features.

41. The at least one non-transitory machine-readable medium of claim 33 further comprising at least one instruction that when executed by the at least one processor causes the at least one processor to perform at least one operation comprising:

including the fixation index in the set of features; and applying the logistic regression model to the set of features including the fixation index, wherein the trained logistic regression model is capable of outputting variant pathogenicity estimates that satisfy the at least one second performance criterion based on the set of features including the fixation index.

42. At least one non-transitory machine-readable medium comprising at least one instruction that when executed by at least one processor causes the at least one processor to perform operations comprising:

applying a logistic regression model to a first set of population data for a first set of genes, wherein an item of the first set of population data comprises, for a variant located at a position within a gene of the first set of genes, a set of features comprising at least one population frequency meta-feature and a reference label that indicates whether the variant is benign or pathogenic, wherein the at least one population frequency meta-feature quantifies predictive value of allele frequency in the gene;

for each item of the first set of population data, evaluating a variant classification prediction output by the logistic regression model based on an expected variant classification indicated by the reference label;

adjusting a value of at least one parameter or coefficient of the logistic regression model until at least one first performance criterion is satisfied to produce a trained logistic regression model, wherein the trained logistic regression model is capable of outputting variant pathogenicity estimates that satisfy at least one second performance criterion;

computing, for a variant, a mathematical combination of subpopulation frequency data and population frequency data; and applying the logistic regression model to the set of features including the mathematical combination of subpopulation frequency data and population frequency data, wherein the trained logistic regression model is capable of outputting variant pathogenicity estimates that satisfy the at least one second performance criterion based on the set of features including the mathematical combination of subpopulation frequency data and population frequency data.

43. The at least one non-transitory machine-readable medium of claim 33, wherein adjusting the value of at least one parameter of the logistic regression model comprises adjusting a C value of the logistic regression model until output of a loss function satisfies the at least one first performance criterion, to produce the trained logistic regression model.

44. The at least one non-transitory machine-readable medium of claim 33, further comprising at least one instruction that when executed by the at least one processor causes the at least one processor to perform at least one operation comprising:

configuring the logistic regression model to model population frequency for variant classification using L1 regularization.

45. The at least one non-transitory machine-readable medium of claim 33, further comprising at least one instruction that when executed by the at least one processor causes the at least one processor to perform at least one operation comprising:

estimating the at least one first performance criterion using a means square error or area under the receiver operating characteristic curve.

46. The at least one non-transitory machine-readable medium of claim 33, further comprising at least one instruction that when executed by the at least one processor causes the at least one processor to perform at least one operation comprising:

determining the second performance criterion using at least one of decision boundary inspection, feature weight inspection, or a comparison to a benchmark variant classification.

47. The at least one non-transitory machine-readable medium of claim 33, further comprising at least one instruction that when executed by the at least one processor causes the at least one processor to perform at least one operation comprising:

using variant classification estimates output by the trained logistic regression model as an input to a variant classification framework.

48. The at least one non-transitory machine-readable medium of claim 33, wherein the at least one population frequency meta-feature comprises expected frequency distributions of known benign variants and known pathogenic variants within the gene.

\* \* \* \* \*